United States Patent
Rosowsky et al.

(10) Patent No.: US 7,119,095 B2
(45) Date of Patent: Oct. 10, 2006

(54) PHARMACEUTICALLY ACTIVE COMPOUNDS AND METHODS OF USE THEREOF

(75) Inventors: Andre Rosowsky, Needham, MA (US); Ronald A. Forsch, Brookline, MA (US)

(73) Assignee: Dana Farber Cancer Institute, Boston, MA (US)

( * ) Notice: Subject to any disclaimer, the term of this patent is extended or adjusted under 35 U.S.C. 154(b) by 0 days.

(21) Appl. No.: 10/848,094

(22) Filed: May 17, 2004

(65) Prior Publication Data

US 2004/0242614 A1    Dec. 2, 2004

Related U.S. Application Data

(63) Continuation of application No. PCT/US02/37155, filed on Nov. 19, 2002.

(60) Provisional application No. 60/334,167, filed on Nov. 20, 2001.

(51) Int. Cl.
| | |
|---|---|
| *C07D 239/48* | (2006.01) |
| *C07D 239/95* | (2006.01) |
| *C07D 471/04* | (2006.01) |
| *A61K 31/506* | (2006.01) |
| *A61K 31/517* | (2006.01) |
| *A61K 31/519* | (2006.01) |
| *A61P 31/06* | (2006.01) |
| *A61P 33/02* | (2006.01) |
| *A61P 33/06* | (2006.01) |
| *A61P 31/08* | (2006.01) |

(52) U.S. Cl. ............... 514/264.1; 514/275; 544/279; 544/283; 544/323

(58) Field of Classification Search ............ 544/279, 544/283, 323, 326; 514/264.1, 275, 264
See application file for complete search history.

(56) References Cited

U.S. PATENT DOCUMENTS

| 3,715,357 A | 2/1973 | Rey-Bellet et al. ...... 260/256.4 |
|---|---|---|
| 5,736,547 A | 4/1998 | Gangjee ..................... 514/258 |

FOREIGN PATENT DOCUMENTS

| EP | 278686 A1 * | 8/1988 |
|---|---|---|
| GB | 1256849 * | 12/1971 |
| GB | 1346710 * | 2/1974 |

OTHER PUBLICATIONS

Snyder et al., J. Med. Liban 48(4): 208-214, 2000.*
Kuyper et al. J. Med. Chem, 28: 303-311, 1985.*

* cited by examiner

*Primary Examiner*—Venkataraman Balasubramanian
(74) *Attorney, Agent, or Firm*—Peter F. Corless, Esq.; Edwards Angell Palmer & Dodge LLP

(57) ABSTRACT

The present invention relates to dihydrofolate reductase inhibitors having an aromatic group and a heteroaromatic group linked by a methylene group; and methods of treatment and pharmaceutical compositions that utilize or comprise one or more of such dihydrofolate reductase inhibitors.

30 Claims, No Drawings

PHARMACEUTICALLY ACTIVE COMPOUNDS AND METHODS OF USE THEREOF

CROSS-REFERENCE TO RELATED APPLICATION

This application is a continuation of copending international patent application PCT/US02/37155, filed on Nov. 19, 2002, which application designates the U.S. and claims priority from U.S. Provisional Patent Application 60/334,167, filed Nov. 20, 2001, which is incorporated by reference.

This invention was made with government support under Grant RO1-AI-29904 from the National Institute of Allergy and Infectious Disease. The government has certain rights in the invention.

BACKGROUND OF THE INVENTION

1. Field of the Invention

The present invention provides new pharmaceutically active compounds, particularly compounds where a diamino substituted heterocyclic moiety is linked via a methylene group to a substituted aryl group. Preferred compounds of the invention include substituted pyrimidine compounds and can exhibit dihydrofolate reductase (DHFR) inhibition activity.

2. Background

Trimethoprim (1, TMP) and piritrexim (2, PTX) are lipid-soluble antifolates that have been used clinically for the prophylaxis and treatment of *Pneumocystis carinii* and *Toxoplasma gondii* infections in patients with AIDS (Klepser, M. E.; Klepser, T. B. *Drugs* 1997; 53, 40–73). TMP was developed over 40 years ago as an antibacterial drug and continues to be widely prescribed, generally in combination with a sulfonamide such as sulfamethoxazole (this combination, also called co-trimoxazole, is popularly known as Bactrim®). A number of clinical studies evaluating a variety of TMP-sulfa drug combinations for treatment or prevention of life-threatening *P. carinii* and *T. gondii* infections in AIDS have been reported in the past decade ((a) Fischl, M. A.; Dickinson, G. M.; La Voie, L. *J. Am. Med. Assoc.* 1988; 259, 1185–1189; (b) Medina, I.; Mills, J.; Leoung, G.; Hopewell, P. C.; Lee, B.; Modin, G.; Benowitz, N.; Wofsy, C. B. *N. Engl. J. Med.* 1990; 323, 776–782; (c) Hughes, W.; Leoung, G.; Kramer, F.; Bozzette, S. A.; Safrin, S.; Frame, P.; Clumeck, N.; Mazur, H.; Lancaster, D.; Chan, C.; Lavelle, J.; Rosenstock, J.; Falloon, J.; Feinberg, J.; LaFon, S.; Rogers, M.; Sattler, F. *N. Engl. J. Med.* 1993; 328, 1521–1527; (d) Safrin, S.; Finkelstein, D. M.; Feinberg, J.; Frame, P.; Simpson, G.; Su, A.; Cheung, T.; Soeiro, R.; Hojczyk, P.; Black J. R. ACTG 108 Study Group, *Ann. Intern. Med.* 1996; 124, 702–802; (e). *Eur J. Clin. Microbiol. Infect. Dis.* 1992; 11, 12–130; (f) Podzamczer, D.; Salazar, A.; Jimenez, J.; Consiglio, E.; Santin, M.; Casanova, A.; Rufi, G.; Gudiol, F. *Ann. Intern. Med.* 1995; 122, 755–781; and (g) Antinori, A.; Murri, R.; Ammassari, A.; De Luca, A.; Linzalone, A.; Cingolani, A.; Damiano, F.; Mauro, G.; Vecchiet, J.; Scoppettuolo, G. *AIDS* 1995; 9, 1343–1350).

Co-trimoxazole is relatively inexpensive, and thus plays an especially important role in controlling AIDS opportunistic infections in economically disadvantaged countries. Initially developed as an anticancer drug, PTX has recently shown some promise against head-and-neck squamous cell carcinoma and bladder carcinomas and has been the subject of one limited clinical study against *P. carinii* pneumonia in patients with AIDS ((a) Uen, W. C; Huang, A. T.; Mennel, R.; Jones, S. E. Spaulding, M. B.; Killion, K.; Havlin, K.; Keegan, P. Clendeninn, N. J. *Cancer* 1992; 69, 1008–1011; (b) Schiesel, J. D.; Carabasi, M.; Magill, G.; Casper, E.; Cheng, E.; Marks, L.; Feyzi, J.; Clendeninn, N. J.; Smalley, R. V. *Invest. New Drugs* 1992; 10, 97–98; (c) Roth B. J. *Semin. Oncol.* 1996; 23: 633–644; (d) Khorsand, M.; Lange, J.; Feun, L. G.; Clendeninn, N. J.; Collier, M.; Wilding, G. *Invest. New Drugs* 1997; 15 157–163). Both TMP and PTX have as their target the enzyme dihydrofolate reductase (DHFR), which plays a ubiquitous role in one-carbon metabolism by mediating the biosynthesis of DNA, RNA, and the essential amino acid methionine (Schweitzer, B. I.; Dicker, A. P.; Bertino, J. R. *FASEB J.* 1990; 4, 2441–2452).

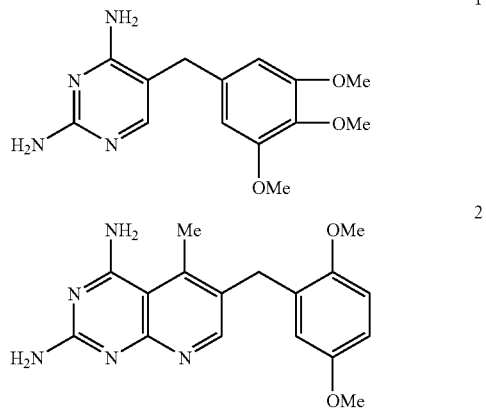

In Kuyper et al., *J. Med. Chem.* 1985; 28, 303–311, a series of compounds were reported in one of the earliest examples of rational structure-based design of DHFR inhibitors. In a series of trimethoprim analogs where the 3'-OMe group was replaced by O-(ω-carboxyalkyl) substituents having up to six $CH_2$ groups, inhibition assays against *E. coli* DHFR revealed a progressive decrease in the $K_i$ values from 2.6 nM to 0.035 nM as the number of $CH_2$ groups was increased from 1 to 3, followed by stabilization of the $K_i$ in the 0.025–0.066 nM range as this number was increased from 3 to 6. The highest affinity for *E coli* DHFR was observed with the O-(5-carboxypentyl) analog 18.

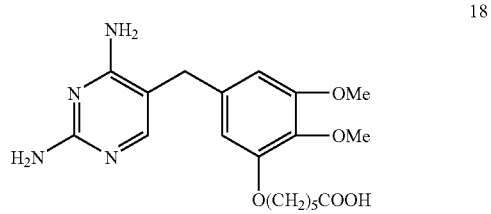

The published literature contains hundreds of mono-, di-, and tricyclic 2,4-diaminopyrimidines that are more potent than trimethoprim, 1, as inhibitors of *P. carinii* versus rat DHFR, but a careful search reveals only a handful whose selectivity and potency are both greater than those of trimethoprim, 1, (FIG. 1). These include the trimethoprim analog 19 (epiroprim, Ro11-8958), the pyrimethamine analogs 20 and 21, the purine 22, the furo[2,3-d]pyrimidines 23 and 24, and the pteridines 25 and 26. See, for example, (a) Then, R. L.; Hartman, P. G.; Kompis, I.; Stephan-Güldner, M; Stöckel, K. Epiroprim. *Drugs Future* 1994; 19, 446–449. (b) Chang, H. R.; Arsenijevic D.; Comte, R; Polak, A.; Then, R. L.; Pechere, J. C. *Antimicrob. Agents Chemother*. 1994; 38, 1803–1807. (c) Martinez, A.; Allegra, C. J.; Kovacs, J. A. *Am. J. Trop. Med. Hyg.* 1996; 54, 249–252. (d) Locher, H. H.; Schlunegger, H.; Hartman, P. G.; Angehm, P.; Then, R. L. *Antimicrob. Agents Chemother*. 1996; 40, 1376–1381. (e) Queener, S. F. *J. Med. Chem.* 1995; 4739–4758. (f) Gangjee, A.; Vasudevan, A.; Queener, S. F.; Kisliuk, R. L. *J. Med. Chem.* 1996; 39, 1438–1446. (g) Kuyper L. F.; Roth, B.; Baccanari, D. P.; Ferone, R.; Beddell, C. R.; Champness, J. N.; Stammers, D. K.; Dann, J. G.; Norrington, F. E. A.; Baker, D. J.; Goodford, P. J. *J. Med. Chem.* 1985; 28, 303–311. (h) Stevens, M. F. G.; Phillip, K. S.; Rathbone, D. L.; O'Shea, D. M.; Queener, S. F.; Schwalbe, C. H.; Lambert, P. A. *J. Med. Chem.* 1997, 40, 1886–1893. (h) Gangjee, A.; Vasudevan, A.; Queener, S. F. *J. Med. Chem.* 1997, 40, 3032–3039. (i) Gangjee, A.; Guo, X.; Queener, S. F.; Galitsky, N.; Luft, J.; Pangbom, W. *J. Med. Chem.* 1998; 44, 1263–1271. (j) Piper, J. R.; Johnson, C. A.; Krauth, C. A.; Carter, R. L.; Hosmer, C. A.; Queener, S. F.; Borotz, S. E.; Pfefferkorn, E. R. *J. Med. Chem.* 1996; 39, 1271–1280. (k) Rosowsky, A.; Cody, V.; Galitsky, N.; Fu, H.; Papoulis, A. T.; Queener, S. F. *J. Med. Chem.* 1999; 42, 4853–4860.

FIGURE 1.
Structures of P. carinii DHFR inhibitors reported to be more potent as well as more selective than trimethoprim (1).

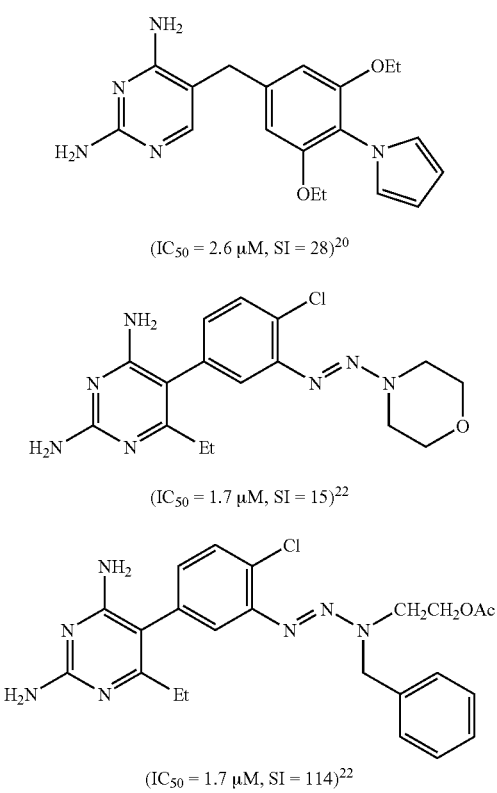

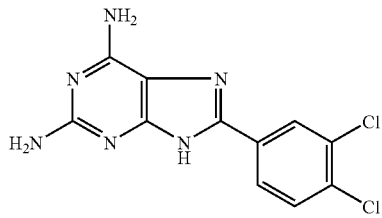

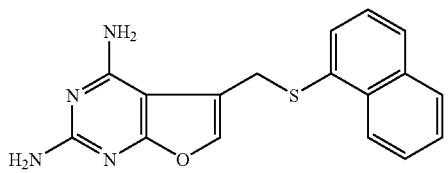

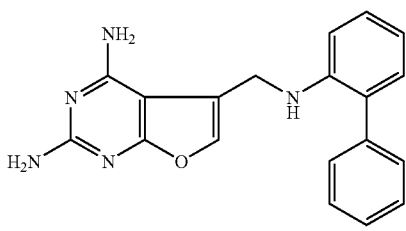

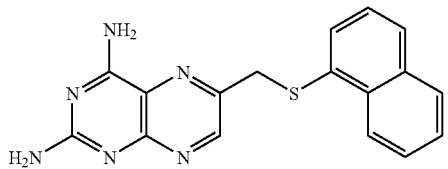

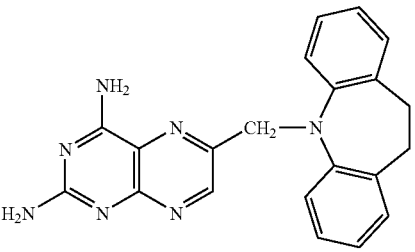

It would be desirable to have new biologically active DHFR inhibitors, particularly DHFR inhibitors which have selective activity against parasitic DHFR enzymes.

SUMMARY OF THE INVENTION

We have now discovered a new class of dihydrofolate reductase (DHFR) inhibitors, pharmaceutical compositions thereof and methods of inhibiting DHFR activity. The present invention also features methods of treating parasitic infections by administering a patient suffering from or susceptible to a parasitic infection a compound which selectively inhibits DHFR enzymes from parasites such as *Pneumocystis carinii, Toxoplasma gondii, Mycobacterium avium.* The compounds of the invention combine the high potency of piritrexim and the selectivity for binding to parasitic DHFR enzymes of trimethoprim. The invention features compounds with a hybrid structure embodying some features of both trimethoprim and piritrexim. The compounds of the invention possess a superior combination of potency and selectivity thatn either parent drug, e.g., trimethoprim or piritrexim.

The present invention features compounds according to the general formula:

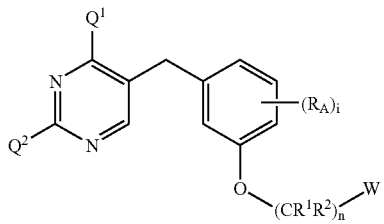

wherein:

$Q^1$ and $Q^2$ are independently selected at each occurrence of $Q^1$ and $Q^2$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, amino, mono and di($C_{1-6}$alkyl) amino, nitrile, carboxamide, hydroxy, thiol, and $C_{1-6}$alkylthio, with the proviso that at least one of $Q^1$, or $Q^2$ is not hydrogen;

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl) amino, nitrile, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio, optionally substituted aryl acetoxy or optionally substituted heteroaryl acetoxy;

$R^1$ and $R^2$ are independently selected at each occurrence of $R^1$, and $R^2$ in Formula I from the group consisting of hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, $C_{1-6}$alkylthio, optionally substituted arylthio, or optionally substituted arylalkylthio;

W is hydrogen, alkoxy, amino, carboxylate, $C_{1-6}$alkylcarbonyloxy, sulfonate or carboxamide;

i is an integer from 0 to about 4; and n is an integer from about 1 to about 12.

The present invention also features compounds according to the general formula:

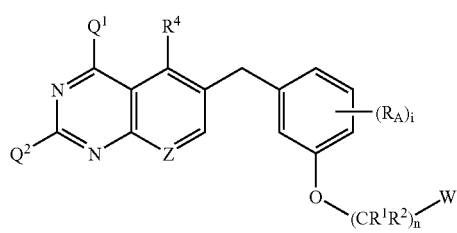

wherein:

$Q^1$ and $Q^2$ are independently selected at each occurrence of $Q^1$ and $Q^2$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, amino, mono and di($C_{1-6}$alkyl) amino, nitrile, carboxamide, hydroxy, thiol, and $C_{1-6}$alkylthio, with the proviso that at least one of $Q^1$ or $Q^2$ is not hydrogen;

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl) amino, nitrile, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio, optionally substituted aryl acetoxy or optionally substituted heteroaryl acetoxy;

$R^1$, $R^2$ and $R^4$ are independently selected at each occurrence of $R^1$, $R^2$ and $R^4$ in Formula I from the group consisting of hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, $C_{1-6}$alkylthio, optionally substituted arylthio, or optionally substituted arylalkylthio;

W is hydrogen, alkoxy, amino, carboxylate, $C_{1-6}$alkylcarbonyloxy, sulfonate or carboxamide;

i is an integer from 0 to about 4; and n is an integer from about 1 to about 12.

In preferred embodiments, the present invention features compounds according to Formula I:

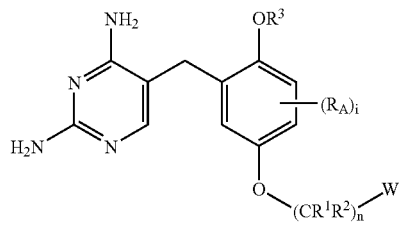

wherein:

$R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl) amino, nitrile, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio, optionally substituted aryl acetoxy or optionally substituted heteroaryl acetoxy;

$R^1$ and $R^2$ are independently selected at each occurrence of $R^1$, and $R^2$ in Formula I from the group consisting of hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio;

$R^3$ is selected from the group consisting of hydrogen, $C_{1-6}$alkyl, $C_{2-6}$alkenyl, $C_{2-6}$alkynyl, and $C_{1-6}$fluoroalkyl;

W is hydrogen, alkoxy, amino, carboxylate, $C_{1-6}$alkylcarbonyloxy, sulfonate or carboxamide;

i is an integer from 0 to about 3; and n is an integer from about 1 to about 12.

In another preferred embodiments, the present invention also features compounds according to Formula III:

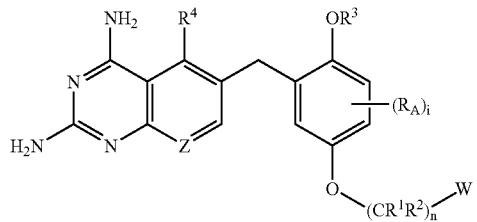

III wherein $R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl) amino, nitrile, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio, optionally substituted aryl acetoxy or optionally substituted heteroaryl acetoxy;

$R^1$, $R^2$, and $R^4$ are independently selected at each occurrence of $R^1$, $R^2$, and $R^4$ in Formula II from the group consisting of hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio;

$R^3$ is selected from the group consisting of hydrogen, $C_{1-6}$alkyl, $C_{2-6}$alkenyl, $C_{2-6}$alkynyl, and $C_{1-6}$fluoroalkyl;

W is hydrogen, alkoxy, amino, carboxylate, $C_{1-6}$alkylcarbonyloxy or carboxamide;

Z is N or CH;

i is an integer from 0 to about 5; and n is an integer from about 1 to about 12.

Preferred compounds compound according to Formula I, Formula III and subformula thereof includes compounds wherein $R_A$ is hydrogen at each occurrence of $R_A$.

Preferred compounds having a —O($CR^1R^2$)$_n$W group meta to the pryrimidyl methyl group include compounds where —O($CR^1R^2$)$_n$W is a $C_{3-12}$alkoxy group or a ω-carboxy$C_{3-12}$alkoxy group. Particularly preferred compounds of the invention include compounds 3a–k.

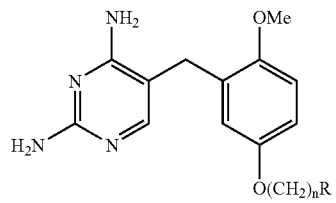

3a–e (R = Me, n = 4–8)
3f–k (R = $CO_2H$, n = 3–8)

Particularly preferred compounds include 3f–k because the omega carboxyl group might interact preferentially with a amino acid residue in the active site of DHFR from the one or more of the parasite species relative to the active site of mammalian DHFR. In addition, the omega-carboxyl group was expected to improve water solubility relative to trimethoprim and piritrexim. Compound 3g, with four $CH_2$ groups in the side chain, e.g., a meta-O—$(CH_2)_4CO_2H$ group, inhibited *P. carinii* DHFR with an $IC_{50}$ of 0.049 microM and rat DHFR with an $IC_{50}$ of 3.9 microM. Its potency against *P. carinii* DHFR was 140-fold greater than that of trimethoprim and close to that of piritrexim, and its binding selectivity for *P. carinii* versus rat DHFR was 8-fold higher than that of trimethoprim and over 10,000 times higher than that of piritrexim. Although it was less potent and less selective against *Toxoplasma gondii* than against *P. carinii* DHFR, it was very potent as well as highly selective against *Mycobacterium avium* MR, with and $IC_{50}$ of 0.0058 microM and a binding selectivity of over 600.

As part of a larger search for lipophilic DHFR inhibitors that would combine the species selectivity of TMP with the potency of PTX (Rosowsky, A.; Papoulis, A. T.; Forsch, R. A.; Queener, S. F. *J. Med. Chem.* 1999; 42, 1007–1017), we were interested in synthesizing analogs of general Formulae I and II including compounds of Formula I of the Formula I-A, in which the 2,4-diaminopyrimidine moiety of TMP was retained but the pattern of substitution in the right-hand benzyl moiety was modified from that of TMP (i.e., 3',4', 5'-trimethoxy) to that of PTX (i.e., 2',5'-dimethoxy). Moreover we postulated, on the basis of reported 3D structures of the ternary complexes of *P. carinii* and mammalian DHFR with TMP and PTX, that replacement of the O-methyl group at the 5'-position by long-chain optionally substituted alkoxy group might increase potency and species selectivity in tandem ((a) Stammers, D. K.; Champness, J. N.; Beddell, C. R.; Dann, J. G.; Eliopoulos, E.; Geddes, A. J.; Ogg, D.; North, A. C. *FEBS Letters* 1987; 218, 178–184. (b) Stammer, D. K.; Delves, C.; Ballantine, S.; Jones, E. Y.; Stuart, D. I.; Achari, A.; Bryant, P. K.; Champness, J. N. *J. Mol. Biol.* 1993; 230, 679–680. (c) Champness, J. H.; Achari; Ballantine, S. P.; Bryant, P. K.; Delves, C. J. Stammers, D. K. *Structure* 1994; 2, 915–924. (d) Kuyper, L. F.; Baccanari, D. P.; Jones, M. L.; Hunter, R. N.; Tansik, R. L.; Joyner, S. S.; Boytos, C. M.; Rudolph, S. K.; Kick, V.; Wilson, H. R.; Caddell, J. M.; Friedman, H. S.; Comley, J. C. W.; Stables, J. N. *J. Med. Chem.* 1996; 39, 892–903). The present invention provides data on the activity, e.g., $IC_{50}$ data, for compounds of Formula I as inhibitors of partially purified preparation of DHFR from rat liver, *P. carinii, T. gondii* and *Mycobacterium avium* (the parasite responsible for tuberculosis). A number of DHFR inhibitors have been found to inhibit proliferation of *M. avium* in culture or in an animal model, but the potential benefit of lipophilic antifolates in combination with leucovorin and sulfa drugs for the prophylaxis or therapy of opportunistic tuberculosis infection in AIDS patients has not been reported in the literature ((a) Seydel, J. K. *J. Chemother.* 1993; 5, 422–429. (b) Fraser, I; Macintosh, I.; Wilkins, E. G. *Clin. Infect. Dis.* 1994; 19, 211. (c) Shah, L. M.; Meyer, C. C.; Cynamon, M. H. *Antimicrob. Agents Chemother.* 1996; 40, 2426–2427. (d) Shoen, C. M.; Choromanska, O.; Reynolds, R. C.; Piper, J. R.; Johnson, C. A.; Cynamon, M. H. *Antimicrob. Agents Chemother.* 1998; 42, 3315–3316. (e) Suling, W. J.; Reynolds, R. C.; Barrow, E. W.; Wilson, L. N.; Piper, J. R.; Barrow, W. W. *J. Antimicrob. Chemother.* 1998 42, 811–815. (f) Suling, W. J.; Seitz, L. E.; Pathak, V.; Westbrook, L.; Barrow, E. W.; Zywno-Van-Ginkel, S.; Reynolds, R. C.; Piper, J. R.; Barrow, W. W. *Antimicrob. Agents Chemother.* 2000; 44, 2784–2793).

DHFR inhibitors of the invention have a broad range of therapeutic applications as antibacterial, antiparasitic, and anticancer agents. Among the parasitic diseases that can be treated with these compounds are malaria, trypanosomiasis, leprosy, toxoplasmosis, and *pneumocystis carinii* pneumonia. The latter two are major opportunistic infections in AIDS patients and individuals with other severe immunodeficiency. DHFR inhibitors are also of potential inhibitors as agricultural chemicals (herbicides, fungicides, etc.)

Preferred compounds of Formula I are inhibitors of dihydrofolate reductase, more preferably, lipophilic inhibitors of dihydrofolate reductase which are suitable for anti-parasitic therapies, especially anti-*Pneumocystis carinii* (Pc) and anti-*Toxoplasma gondii* (Tg) therapy, particularly in immunocompromised patients such as HIV-positive subjects.

The invention also provides pharmaceutical compositions comprising a compound of the above Formula I suitable together with a pharmaceutically acceptable carrier.

Other aspects of the invention are discussed infra.

DETAILED DESCRIPTION OF THE INVENTION

Additional preferred compounds according to Formula I include compounds according of the Formula II:

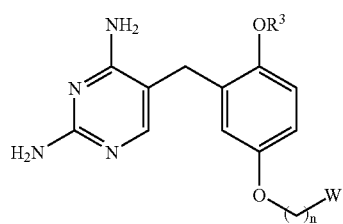

wherein
W is hydrogen, hydroxy or carboxylate;
$R^3$ is a $C_{1-4}$alkyl group; and
n is an integer from about 3 to about 8.

Preferred compounds of the invention include those compounds of Formula III according to Formula IV and V:

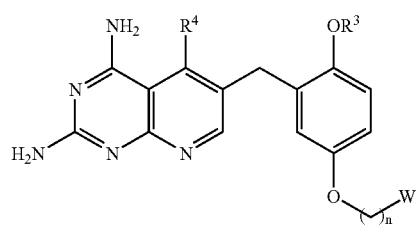

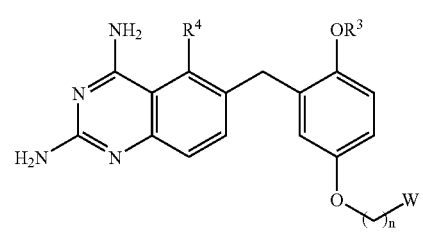

wherein
W is hydrogen, hydroxy or carboxylate;
$R^3$ is a $C_{1-4}$alkyl group;
$R^4$ is hydrogen, chloro, methoxy or methyl; and
n is an integer from about 3 to about 8.

Additional preferred compounds according to any one of Formula I to V include those compounds where W is carboxylate or where W is hydrogen.

Other preferred compounds of the invention according to Formula I to V include those compounds having an $IC_{50}$ of 50 µM or less against a DHFR enzyme. More preferably, compounds of the invention have an $IC_{50}$ of 25 µM, 10 µM, 5 µM, 1 µM, or 0.5 µM or less against a DHFR enzyme. Most preferred compounds have an $IC_{50}$ of 50 µM, 25 µM, 10 µM, 5 µM, 1 µM, or 0.5 µM or less against a parasitic DHFR enzyme.

Particularly preferred compounds include those with an $IC_{50}$ of 25 µM, 10 µM, 5 µM, 1 µM, or 0.5 µM or less against a DHFR enzyme of a parasite capable of causing a disease or infection in a mammal, particularly a mammal which is HIV-positivie or is susceptible to or suffering from AIDS. Typical parasites which compounds of the invention are preferably active against include those parasites causing malaria, trypanosomiasis, leprosy, toxoplasmosis, and *pneumocystis carinii* pneumonia such as *Pneumocystis carinii, Toxoplasma gondii*, and *Mycobacterium avium*.

Other preferred compounds of the invention exhibit increased activity against DHFR enzymes from parasites relative to DHFR enzymes from mammals. Preferred compounds of the invention including compounds of Formula I–V have a binding selectivity of the compound, e.g., the ratio of the compound's $IC_{50}$ for binding mammalian DHFR enzymes to the compound's $IC_{50}$ for binding $IC_{50}$ for binding parasitic DHFR enzymes, which is about 1 or more. More preferably the binding selectivity is about 2 or more, about 4 or more, about 8 or more, or more, about 16 or more, about 20 or more, or about 50 or more.

The present invention also features pharmaceutical compositions comprising a compound of any one of Formula I–V and a pharmaceutically acceptable carrier.

Suitable halogen substituent groups or halide groups of compounds of the invention, including compounds of Formula I, II, III, IV, and V as defined above, include F, Cl, Br and I. Alkyl groups of compounds of the invention preferably have from 1 to about 12 carbon atoms, more preferably 1 to about 8 carbon atoms, still more preferably 1 to about 6 carbon atoms. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups, particularly branched chain groups such as isopropyl and t-butyl. Preferred alkenyl groups of compounds of the invention have one or more unsaturated linkages and from 2 to about 12 carbon atoms. more preferably 2 to about 8 carbon atoms, still more preferably 2 to about 6 carbon atoms. The term alkenyl as used herein refer to both cyclic and noncyclic groups, although straight or branched noncyclic groups are generally more preferred, particularly branched chain groups. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms. Preferred thioalkyl groups of compounds of the invention include those groups having one or more thioether linkages and from 1 to about 12 carbon atoms, more preferably from 1 to about 8 carbon atoms, and still more preferably 1 to about 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms. Preferred arylamino groups include those groups having an amino group substituted with one or two aryl groups. Preferred heteroarylamino groups include those groups having an amino group substituted with one or two heteroaryl groups. Substituted and unsubstituted mono and dialkylamino groups are particularly preferred, especially where each alkyl chain of the group has from 1 to about 6 carbon atoms. Preferred alkylsulfoxide of compounds of the invention have one or more sulfoxide groups, more typically one sulfoxide group, and from 1 to about 12 carbon atoms, more preferably 1 to about 8 carbon atoms, still more preferably 1 to about 6 carbon atoms. Preferred sulfonoalkyl groups of compounds of the invention have one or more sulfono ($SO_2$) groups, more typically one or two sulfono groups, and from 1 to about 12 carbon atoms, more preferably 1 to about 8 carbon atoms, still more preferably 1 to about 6 carbon atoms. Preferred alkanoyl groups of compounds of the invention include groups having one or more carbonyl groups, more typically one or two carbonyl groups, and from 1 to about 12 carbon atoms, more preferably 1 to about 8 carbon atoms, still more preferably 1 to about 6 carbon atoms. Preferred alkoxycarbonylamino groups include those groups of the formula —NHCOOR where R is substituted or unsubstituted alkyl having from 1 to about 10 carbon atoms, more preferably 1 to about 6 carbon atoms. Suitable heteroaromatic groups of compounds of the invention contain one or more N, O or S atoms and include, e.g., quinolinyl, pyridyl, pyrazinyl, indolyl, carbazoyl, turyl, pyrrolyl, thienyl, thiazolyl, aminothioazolyl such as 2-aminothiazolyl, pyrazolyl, oxazolyl, imidazolyl, indolyl, benzofuranyl, benzothiazolyl and pyridyl including 2-pyridyls and 4-pyridyls, particularly pyridyl substituted at one or more ring positions by moieties such as hydroxy, alkanoyl such as acetate, alkylaminocarbonyl having from 1 to about 8 carbon atoms and alkoxycarbonyl having from 1 to about 8 carbon atoms. Suitable heteroalicyclic groups of compounds contain one or more N, O or S atoms and include, e.g., aziridinyl, azetidinyl, tetrahydrofuranyl, tetrahydropyranyl, pyrrolidinyl, 1,2,3,6-tetrahydropyridinyl, piperazinyl, piperidinyl, morpholinyl and thiomorpholinyl.

Substituted moieties of compounds of the invention, including substituted $Q^1$, $Q^2$, $R_4$, $R^1$, $R^2$, $R^3$, $R^4$ and W groups, may be "optionally substituted," that is groups may be substituted at one or more available positions by one or more suitable groups such as, e.g., halogen such as fluoro, chloro, bromo and iodo; cyano; hydroxyl; nitro; alkyl groups including those groups having 1 to about 12 carbon atoms or from 1 to about 6 carbon atoms, preferably noncyclic alkyl groups including branched chain groups such as isopropyl and t-butyl; alkenyl and alkynyl groups including groups having one or more unsaturated linkages and from 2 to about 12 carbon or from 2 to about 6 carbon atoms; alkylthio groups including those moieties having one or more thioether linkages and from 1 to about 12 carbon atoms or from 1 to about 6 carbon atoms; and, in at least preferred aspects of the invention, alkoxy groups having those having one or more oxygen linkages and from 1 to about 12 carbon atoms or 1 to about 6 carbon atoms; and aminoalkyl groups such as groups having one or more N atoms (which can be present as primary, secondary and/or tertiary N groups) and from 1 to about 12 carbon atoms or from 1 to about 6 carbon atoms.

Particularly preferred substituent groups of compounds of the invention, including compounds of Formulae I, II, III, IV, and V include nitrogen containing groups including aminoalkyl, alkoxycarbonylamino and nitrogen-containing heteroaromatic and heteroalicyclic groups. Preferred nitrogen-containing cyclic groups include those moieties that have one or two heteroatoms, e.g. one or two N, O, or S atoms.

Chemistry: Synthesis of Compounds According to Formula I

As shown in Scheme 1, treatment of 4-methoxyphenol (4) with methyl chloroformate in the presence of pyridine afforded the carbonate ester 5 (92% yield), which on reaction with $MeOCHCl_2$ and $TiCl_4$ as described earlier was converted to the masked aldehyde 6 (Scarpati M. L.; Bianco, A.; Mascitelli, L.; Passacantilli, P. *Synth. Commun.* 1990; 20, 2565–2572). On treatment with HCl at 0° C. for 30 min, compound 6 underwent cleavage to aldehyde 7. More vigorous acidolysis of 7 cleaved the carbonate ester to form the phenol 8, and further reaction with 1-bromopentane in the presence of $K_2CO_3$ in DMSO solution afforded the previously unknown ether 9. Condensation of 9 with 3-morpholinopropionitrile in anhydrous DMSO containing a catalytic amount of NaOMe[17a] led to the 3-morpholinoacrylonitrile 10, which on sequential beating with aniline hydrochloride and by guanidine (Stuart, A. Paterson, T.; Roth, B.; Aig, E. *J. Med. Chem.* 1983; 26, 667–673). was converted into 2,4-diamino-5-[(2-methoxy-5-pentyloxy)benzyl]pyrimidine (3a) via the 3-anilinoacrylonitrile 11. Exchange of the morpholino group by an anilino group was an essential step in the sequence, as 10 itself failed to undergo cyclization with guanidine. Compounds 10 and 11 were each used without purification. The overall yield of 3a for the 7 steps starting from 4 was 30%. The final product was purified by flash chromatography on silica gel (10:1 EtOAc-MeOH) followed by recrystallization from aqueous EtOH. In addition to other alkyl and aryl proton signals, the $^1$H NMR spectrum of 3a in DMSO-$d_6$ solution featured the expected singlets at δ 3.47 for the $CH_2$ group between the phenyl and pyrimidine rings, δ 3.73 for the 2-OMe group, and δ 7.39 for the $C^7$ proton on the pyrimidine ring.

Although the synthesis of 3a as described above was workable, we felt that an improvement would be to use NaOMe for the deprotection of 7. We reasoned that cleavage of the carbonate protecting group would afford a DMSO-soluble Na salt of the phenol that could be alkylated directly. Thus, 7 was treated with one equivalent of NaOMe in MeOH at room temperature, the solution was evaporated to dryness, and the residue was triturated with $Et_2O$ to obtain the Na salt (12) as a solid. After being dried thoroughly under vacuum, the solid was dissolved in dry DMSO and allowed to react with 1-bromohexane at room temperature to obtain the O-hexyl derivative of 8, which was then subjected to the same sequence of steps as 9 (cf. Scheme 1) to obtain 2,4-diamino-5-[(2-methoxy-5-hexyloxy)benzyl]pyrimidine (3b) with a five-step yield of 58% starting from 8. The same improved sequence using other bromoalkanes afforded the longer-chain analogs 3c–e in overall yields of 63% (3c), 58% (3d), and 47% (3e).

Because of a concern that the strongly basic condensation reactions in Scheme 1 might cause side reactions involving the α-CH₂ or carbonyl group, a somewhat different sequence of steps was followed to obtain the carboxy analogs 3f–k. Thus, as shown in Scheme 2, compound 8 was converted to 12 with NaOMe in MeOH, the dried salt was condensed with benzyl bromide in DMSO, and the resulting O-benzyl derivative 13a was converted to the previously unknown diaminopyrimidine 14a (59% yield), from which we had intended to cleave the O-benzyl group by catalytic hydrogenolysis over Pd—C. In the event, this debenzylation proved quite difficult, and we therefore abandoned 14a in favor of the O-(4-methoxybenzyl) derivative 14b, which formed in better yield (70%) and was easily converted to the diaminopyrimidine 15b (61% yield) via the same series of reactions. When 14b was left to stand for 2 days at room temperature in MeOH solution containing a two-fold excess of TsOH.H₂0, it was converted to 2,4-diamino-5-[(2-methoxy-5-hydroxy)benzyl]pyrimidine (15) in 89% yield. The Na salt 16 was then generated with a stoichiometric amount of NaOEt in EtOH and isolated by evaporation of the solvent. After being rigorously dried in vacuum, 16 was taken up in dry DMSO and allowed to react with one equivalent of ethyl 5-bromopentanoate at room temperature while monitoring the progress of the reaction by TLC (silica gel, 5:1 EtOAc-MeOH). The resulting ester 17 (n=5) was saponified by addition of a twofold excess of NaOH directly to the alkylation mixture, and the resulting acid 3g was purified by column chromatography on Dowex 50W-X2 sulfonic acid resin using 1.5% NH₄OH as the eluent. Freeze-drying of appropriately pooled fractions followed by re-dissolution in a minimal volume of dilute NH₄OH and acidification with 10% AcOH afforded the product as an off-white powder, usually solvated with either AcOH and/or H₂O. Purification by ion-exchange chromatography on a DEAE-cellulose (HCO₃⁻ form) was also tried but was found to be much less satisfactory due to poor solubility. The same sequence of steps was also used to obtain 3f and 3h–k from other bromo esters via 17 (n=3) and 17 (n=4, 6–8) with an overall two-step yield of 65–85% based on 15. The identity of each product was confirmed by ¹H NMR and by microanalysis. As with 3a–e, characteristic singlets were observed at δ 3.46, 3.72, and 7.37, and where solvation with AcOH was indicated by microanalysis, an extra singlet not assignable to protons in the diaminopyrimidine derivative was observed at δ1.88. It may be noted that Scheme 2 should, in principle, be applicable to the synthesis of 3a–e, but was not used for this purpose because adequate amounts of the simple O-alkyl analogs for in vitro testing had already been made via Scheme 1.

Scheme 1

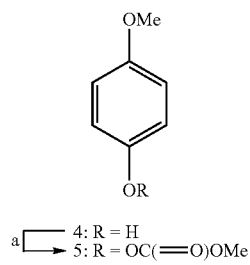

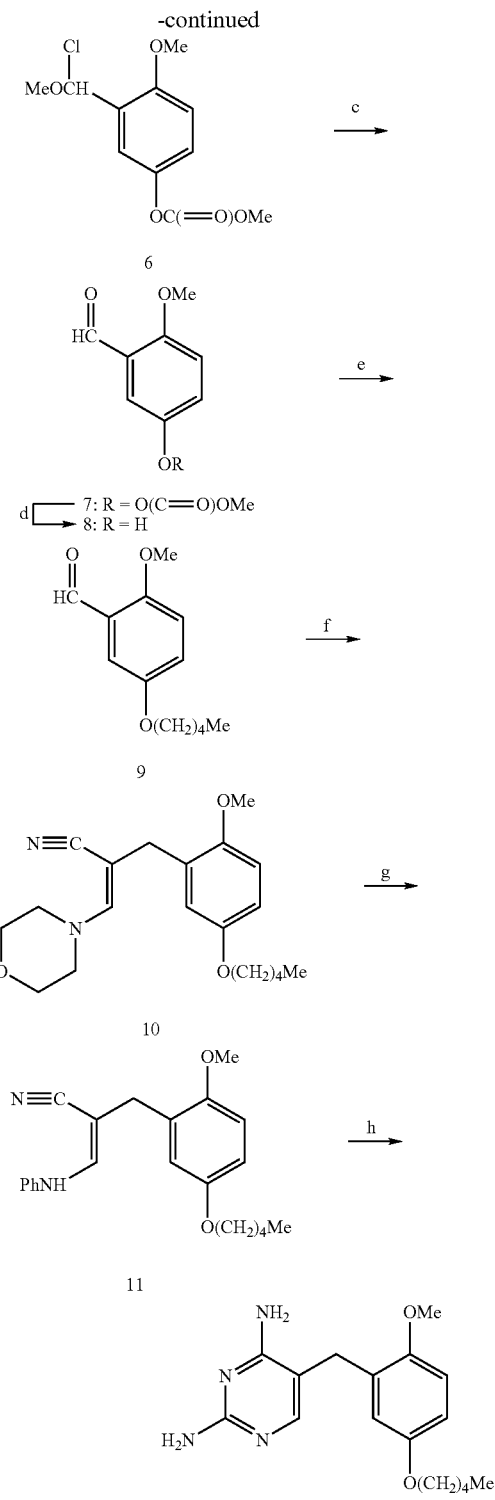

Reagents:
a) MeOC(=O)Cl/C₅H₅N;
b) MeOCHCl₂/TiCl₄;
c) HCl, 0° C.;
d) HCl/MeOH, reflux;
e) Br(CH₂)₅Me/K₂CO₃/DMSO;
f) 3-Morpholinopropanenitrile/NaOMe/DMSO;
g) PhNH₂˙HCl/EtOH;
h) H₂NC(=NH)NH₂/EtOH

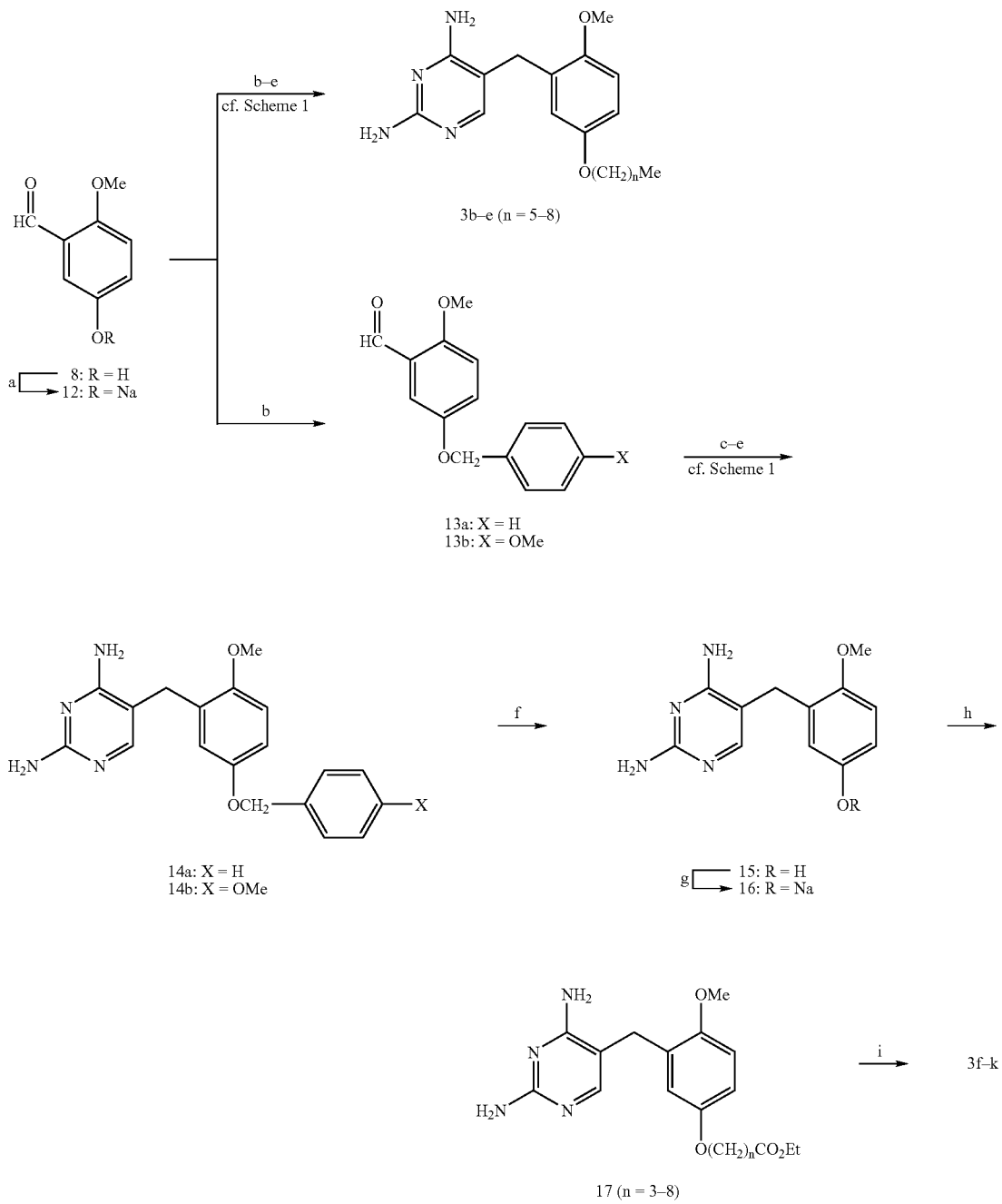

Scheme 2

Enzyme Inhibition

Alternatively compounds of Formula I may be prepared by synthetic methods including a transition metal mediated cross-coupling of a heteroaryl bromide or a heteroaryl iodide with a substituted benzyl zinc halide as a key reaction step. See, for example, Rosowsky et al., *J. Org. Chem.*, 2001, v. 66, pp 7522–7526.

Compounds of Formula I including preferred compounds 3a–k were tested for their ability to inhibit DHFR from *P. carinii, T. gondii, M. avium*, and rat liver using a literature assay (Broughton, M. C.; Queener, S. F. *Pneumocystis carinii* dihydrofolate reductase used to screen potential antipneumocystis drugs. *Antimicrob. Agents Chemother.* 1991; 35, 1348–1355. (c) Chio, L.-C.; Queener, S. F. Identification of highly potent and selective inhibitor of *Toxoplasma gondii* dihydrofolate reductase. *Antimicrob. Agents Chemother.* 1993; 37, 1914–1923 along with selectivity index (SI) values determined from the ratio $IC_{50}$(rat liver/ $IC_{50}$ (*P. carinii, T. gondii*, or *M. avium*). The results are shown in Table 1, with previously reported data for trimethoprim (1) and piritrexim (2) also presented for comparison.

TABLE 1

Inhibition of P. carinii, T. gondii, M. avium and rat liver DHFR by 2,4-diamino-5-[2-methoxy-5-(long-chain alkoxy and ω-carboxyalkoxy)benzyl]pyrimidines

| Cmpd | IC$_{50}$ (μM) | | | | SI$^a$ | | |
|---|---|---|---|---|---|---|---|
| | P. carinii | T. gondii | M. avium | Rat liver | P. carinii | T. gondii | M. avium |
| 1 | 12 | 2.7 | 0.19 | 130 | 11 | 44 | 680 |
| 2 | 0.031 | 0.017 | ND | 0.0015 | 0.0048 | 0.088 | ND |
| 3a | 19 | 6.5 | 0.31 | 44 | 2.3 | 6.8 | 140 |
| 3b | 14 | 9.2 | 0.39 | 29 | 2.1 | 3.1 | 74 |
| 3c | 5.6 | 5.0 | 0.89 | 11 | 1.9 | 2.1 | 12 |
| 3d | 44 | 15 | 3.3 | 30 | 0.69 | 2.0 | 9.1 |
| 3e | 51 | 32 | 32 | 86 | 1.7 | 2.7 | 2.7 |
| 3f | 0.25 | 0.18 | 0.0048 | 2.6 | 11 | 14 | 560 |
| 3g | 0.049 | 0.11 | 0.0058 | 3.9 | 80 | 35 | 660 |
| 3h | 0.80 | 0.48 | 0.15 | 17 | 21 | 35 | 110 |
| 3i | 2.6 | 0.18 | 0.19 | 12 | 4.5 | 65 | 63 |
| 3j | 7.1 | 0.36 | 0.13 | 12 | 1.7 | 33 | 92 |
| 3k | 4.8 | 0.43 | 0.15 | 12 | 2.5 | 28 | 80 |

$^a$SI = IC$_{50}$ (rat liver)/IC$_{50}$ (P. carinii, T. gondii, or M. avium).
$^b$In a separate experiment to confirm the results for 3 g against P. carinii and rat liver DHFR, the IC$_{50}$s were found to be 0.055 and 5.4 μM respectively, giving a calculated SI of 98.
$^c$Results for trimethoprim (1) and piritrexim (2) were obtained under the same standardized assay conditions as 3a-k, (Broughton, M. C.; Queener, S. F. Antimicrob. Agents Chemother. 1991; 35, 1348–1355. Chio, L.-C.; Queener, S. F. Antimicrob. Agents Chemother. 1993; 37, 1914–1923).
ND = not determined.

The most potent of the O-alkyl derivatives against *P. carinii*, *T. gondii*, and rat liver DHFR was compound 3c (n=5), with IC$_{50}$ values of 5.6, 5.0, and 11 μM respectively. Moreover there was an increase in potency against all three enzymes as the length of the 5'-O-alkyl group increased from n=4 to n=6, followed by a decrease in potency as this length increased from n=6 to n=8. However this pattern was slightly different in the case of the *M. avium* enzyme, which tended to be more sensitive than the others. The most potent of the 5'-(O-alkyl) derivatives against this enzyme were 3a (n=4) and 3 b (n=5), with IC$_{50}$ values of 0.31 and 0.39 μM. Interestingly, while 3a–e were only marginally selective for *P. carinii* and *T. gondii* DHFR relative to the rat enzyme, 3a and 3 b were somewhat selective for *M. avium* DHFR, with SI values of 140 and 74.

As can be seen from Table 1, the potency of 3c, the best of the 5'-(O-alkyl) derivatives, was slightly greater against *P. carinii* DHFR than that of 1. However, because 3c inhibited the rat enzyme 12-fold better than trimethoprim, 1, its SI was lower. Moreover, 3c showed even lower selectivity for the *T. gondii* DHFR enzyme. On the other hand, because of the very high potency of piritrexim (2) against rat DHFR, the selectivity of 3c for both the *P. carinii* and the *T. gondii* enzymes relative to piritrexim 2 was improved by at least 10-fold.

The most potent of the 5'-O-(ω-carboxyalkyl) analogs 3f–k against *P. carinii* DHFR was 3g (n=4), with an IC$_{50}$ of 0.049 μM as compared with 12 μM for trimethoprim, 1, and 0.031 μM for piritrexim, 2. Thus, 3g approached the potency of piritrexim 2 against this enzyme, and was 245 times more potent than trimethoprim, 1. As in the 5-(O-alkyl) series, the potency of the 5'-O-(ω-carboxyalkyl) derivatives decreased when n was >4. Moreover the potency of 3f was lower than that of 3g, confirming that the optimal value of n against *P. carinii* DHFR was 4. The carboxyalkyl derivatives 3f–k were also more potent than 3a-e against both *T. gondii* and *M. avium* DHFR. With the exception of 3c, this was also true for inhibition of the rat enzyme. As in the case of the *P. carinii* enzyme, 3g was the best inhibitor of *T. gondii* and *M. avium* DHFR, but was also the best inhibitor of the rat enzyme.

A gratifying aspect of the data in Table 1 was the high selectivity of 3g for *P. carinii* versus rat DHFR. Although a somewhat lower SI was obtained with 3h, both compounds were superior to trimethoprim, 1, and piritrexim 2. The selectivity of 3g for this enzyme (SI=80) was 7-fold greater than that of trimethoprim, 1, (SI=11) and >10$^4$ times greater than that of piritrexim 2 (SI=0.0048), Compound 3g also displayed the highest selectivity of any of the compounds in both the 5'-O-alkyl and 5'-O-(ω-carboxyalkyl) series against the *M. avium* enzyme. Interestingly, the potency of 3g was 33-fold higher than that of trimethoprim, 1, against both the *M. avium* and rat DHFR, and thus there was no difference in SI for the *M. avium* enzyme between these two compounds.

It was of interest to note was that the pattern of selectivity of 3f–k for *T. gondii* versus rat DHFR differed markedly from the pattern against the *P. carinii* and *M. avium* enzymes, in that the most selective compound was 3i rather than 3g, and that the SI was relatively insensitive to the length of the side chain, with 3i (SI=65) being only twice as selective as the other congeners (SI=28–35). Also worth noting is the similarity in potency and selectivity of 3g and piritrexim 2 against *P. carinii* DHFR, which suggests that the activity of this enzyme may share common features not present in the *T. gondii* enzyme. While all three of the parasite enzymes have been cloned and sequenced, only the 3D structure of the *P. carinii* enzyme is published. See, for example, Broughton, M. C.; Queener, S. F. *Antimicrob. Agents Chemother.* 1991; 35, 1348–1355. Chio, L.-C.; Queener, S. F. *Antimicrob. Agents Chemother.* 1993; 37, 1914–1923. Edman, J. C.; Edman, U.; Cao, M.; Lundgren, B.; Kovacs, J. A.; Santi, D. V. *Proc. Nat. Acad. Sci.* 1989; 86, 8625–8629. Roos, D. J. *J. Biol. Chem.* 1993; 268, 6269–6280. Trujillo, M.; Donald, R. G. K.; Roos, D. S.; Greene, P. J.; Santi, D. V. *Biochemistry* 1996; 35, 6366–6374. (c) Zywno van Ginkel, S.; Dooley, T. P.; Suling, W. J.; Barrow, W. W. *FEMS Microbiol. Lett.* 1997; 156, 69–78. Erratum in: *FEMS Microbiol. Lett.* 1998; 158, 279.

The activity of 3g against *M. avium* DHFR was also of interest in view of several recent reports concerning the efficacy of a promising second-generation TMP analog, epiroprim (19, Ro 11-8958, FIG. 1), in combination with a sulfa drug, in the experimental treatment of *P. carinii* and *T. gondii* infection in rodent models. The $IC_{50}$ value and selectivity of 19 against *P. carinii* versus rat liver DHFR are reported to be 2.6 µM and 28 µM, whereas the corresponding values against *T. gondii* versus rat liver DHFR are reported to be 0.47 µM and 155. Thus, 3g appears to be ca. 50-fold more potent and 3-fold more selective than 19 against *P. carinii* DHFR. In contrast, it is only slightly more potent than 19 against the *T. gondii* enzyme but is less selective. Thus compound 3g, which most nearly approaches 20 in terms of having a highly favorable combination of potency and selectivity, joins this small group and thus may be viewed as a promising lead for structure-activity optimization. See, for example, Then, R. L.; Hartman, P. G.; Kompis, I.; Stephan-Güldner, M; Stöckel, K. *Drugs Future* 1994; 19, 446–449. (b) Chang, H. R.; Arsenijevic D.; Comte, R; Polak, A.; Then, R. L.; Pechere, J. C. *Antimicrob. Agents Chemother.* 1994; 38, 1803–1807. (c) Martinez, A.; Allegra, C. J.; Kovacs, J. A. *Am. J. Trop. Med. Hyg.* 1996; 54, 249–252, (d) Locher, H. H.; Schlunegger, H.; Hartman, P. G.; Angehm, P.; Then, R. L. *Antimicrob. Agents Chemother.* 1996; 40, 1376–1381. Queener, S. F. *J. Med. Chem.* 1995; 4739–4758. (b) Gangjee, A.; Vasudevan, A.; Queener, S. F.; Kisliuk, R. L. *J. Med. Chem.* 1996; 39, 1438–1446.

Thus the compounds of the present invention, particularly compounds of Formula I, are useful as pharmaceuticals for the treatment of mammals, including humans, particularly for the treatment of mammals suffering from or susceptible to an immunodeficiency disorder, such as a mammal that is HIV positive, particularly a human suffering from or susceptible to AIDS. Other immuno-comprised subjects also will benefit from the therapies of the invention, such as a subject suffering from an autoimmune disorder and the like.

Compounds of the invention are useful as DHFR inhibitors and are generally useful for in therapeutic applications such as antibacterial applications, antiparasitic applications and anticancer applications. Preferred parasitic diseases which may be treated by administration to a patients suffering from or susceptible to a parasitic disease of one or more compounds of the invention include malaria, trypanosomiasis, leprosy, toxoplasmosis, and pneumocystis carinii pneumonia. Compounds of the invention are particularly useful to combat parasitic infections which are known to inflict HIV-positive or patients suffering from or susceptible to AIDS. Thus, the invention provides a method for the treatment of a subject that is suffering from AIDS, or is otherwise immuno-compromised, the method comprising administration of an effective amount of one or more compounds of the invention in a pharmaceutically useful form, once or several times a day or other appropriate schedule, orally, rectally, parenterally (particularly intravenously), topically, etc.

For such treatment, the compounds of the invention are administered in effective amounts and in appropriate dosage form ultimately at the discretion of the medical or veterinary practitioner. For example, as known to those skilled in the art, the amount of compounds of the invention required to be pharmaceutically effective will vary with a number of factors such as the mammal's weight, age and general health, the efficacy of the particular compound and formulation, route of administration, nature and extent of the condition being treated, and the effect desired. The total daily dose may be given as a single dose, multiple doses, or intravenously for a selected period. Efficacy and suitable dosage of a particular compound can be determined by known methods. ore particularly, for treatment of a tumor in a mammal such as a human, particularly when using more potent compounds of the invention, a suitable effective dose of the compound of the invention will be in the range of 0.1 to 100 milligrams per kilogram body weight of recipient per day, preferably in the range of 1 to 10 milligrams per kilogram body weight of recipient per day. The desired dose is suitably administered once daily, or as several sub-doses, e.g. 2 to 4 sub-doses administered at appropriate intervals through the day, or other appropriate schedule. Such sub-doses may be administered as unit dosage forms, e.g., containing from 0.2 to 200 milligrams of compound(s) of the invention per unit dosage, preferably from 2 to 20 milligrams per unit dosage.

The compounds of the present invention may be suitably administered to a subject as a pharmaceutically acceptable salt. Such salts can be prepared in a number of ways. For example, where the compound comprises a basic group such as an amino group, salts can be formed from an organic or inorganic acid, e.g. hydrochloride, sulfate, hemisulfate, phosphate, nitrate, acetate, oxalate, citrate, maleate, etc.

The therapeutic compound(s) may be administered alone, or as part of a pharmaceutical composition, comprising at least one compound of the invention together with one or more acceptable carriers thereof and optionally other therapeutic ingredients, e.g., other AIDS agents such as a cocktail of therapeutic agents. Possible other therapeutic agents included in such a cocktail include, e.g., AZT, 3TC, and the like as well as other anti-parasitic or anti-biotic agents. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well known in the art of pharmacy.

Such methods include the step of bringing into association the to be administered ingredients with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be presented as ointments, creams, gels and pastes comprising one or more compounds of the present invention and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example, those suitable for oral administration may include flavoring agents.

The following non-limiting examples are illustrative of the invention. All documents mentioned herein are incorporated herein by reference in their entirety.

Experimental Section

IR spectra were obtained on a Perkin-Elmer Model 781 double-beam recording spectrophotometer. Only peaks with wave numbers above 1400 cm$^{-1}$ are reported. $^1$H NMR spectra were recorded at 200 MHz on a Varian VX200 instrument, or in some instances at 60 MHz on a Varian EM360 instrument with Me$_4$Si as the internal standard. Each peak is denoted as a singlet (s), broad singlet (br s), doublet (d), doublet of doublets (dd), triplet (t), or pentet (p). TLC analyses were on Whatman MK6F silica gel plates with UV illumination at 254 nm. Column chromatography was on Baker 7024 flash silica gel (40 μM particle size). Melting points were measured in Pyrex capillary tubes in a Mel-Temp 'Electrothermal' apparatus (Fisher Scientific, Pittsburgh, Pa.), and are not corrected. 3-Morpholinopropionitrile was prepared by adding acrylonitrile dropwise to an equimolar amount of morpholine in an ice-bath, and stirring the mixture at room temperature for 1 h. The resulting light yellow oil was used directly to prepare 13 and other 2-aryl-methyl-3-morpholinoacrylonitriles. Other chemicals were purchased from Sigma-Aldrich (St. Louis, Mo.) or Lancaster Synthesis (Windham, N.H.). Elemental analyses were performed by Quantitative Technologies, Inc. (Whitehouse, N.J.), and were within ±0.4% of theoretical values.

EXAMPLE 1

2-Methoxy-5-pentyloxybenzaldehyde (Scheme 1, Compound 9).

Step 1. A stirred solution of 4 (24.8 g, 0.2 mol) and pyridine (16.6 g, 17 mL, 0.21 mol) in CH$_2$Cl$_2$ (150 mL) was cooled in an ice-bath and treated dropwise with MeOCOCl (19.9 g, 16.2 mL, 0.21 mol) over a period of 15 min. The mixture was then stirred at room temperature for 45 min. After extraction with 1 N HCl, H$_2$O, 0.5 N NaOH, and H$_2$O, the organic solvent was removed by rotary evaporation and the residue distilled under vacuum to obtain 4-(methoxycarbonyloxy)anisole (5) as a colorless liquid which crystallized on prolonged standing, and was used directly in the next step; yield 33.4 g (92%); bp 112° C./0.2 Torr; mp 33–34° C. (lit. mp 34.5–36° C.); $^1$H NMR (200 MHz, CDCl$_3$) δ 3.73 (s, 3H, MeO), 3.83 (s, 3H, MeOCO), 6.85 (d, J=9 Hz, 2H, aryl 3- and 5-H), 7.11 (d, J=9 Hz, 2H, aryl 2- and 6-H).

Step 2. To a stirred solution of 5 (20 g, 0.11 mol) in CH$_2$Cl$_2$ (250 mL) at 0° C. was added TiCl$_4$ (49.2 g, 28.5 mL, 0.26 mol) in CH$_2$Cl$_2$ (50 mL). Stirring was continued at 0° C. while a solution of MeOCHCl$_2$ (14.6 g, 11.5 mL, 0.127 mol) was added dropwise over 30 min. When the addition was complete, the solution was warmed to room temperature, left to stand for 30 min, and concentrated to half-volume by rotary evaporation. The resulting solution, containing the α-chloro ether 6, was poured into a mixture of ice (250 g) and 12 N HCl (10 mL), and then EtOAc (200 mL) was added. The two-phase mixture was stirred vigorously for 30 min, the layers were separated, the aqueous layer was back-extracted with EtOAc, and the combined EtOAc extracts were evaporated to dryness. Recrystallization of the crude solid (24.2 g) from a mixture of isooctane and absolute EtOH afforded 2-methoxy-5-(methoxycarbonyloxy) benzaldehyde (7) as white needles (17.7 g, 77%); mp 88–89° C. (lit. mp 88–90° C. $^1$H NMR (CDCl$_3$) δ 3.90 (s, 3H, MeO), 3.92 (s, 3H, MeO), 6.99 (d, J=9 Hz, 1H, aryl 3-H), 7.38 (dd, J=9 Hz, J=3 Hz, 1H aryl 4-H), 7.63 (d, J=3 Hz, 1H, aryl 6-H), 10.45 (s, 1H, CH=O). Evaporation of the supernatant from the first crop afforded an additional 5.3 g (23%), bringing the total to 23 g (100%). The two fractions were combined and used without further purification.

Step 3. A suspension of the carbonate ester 7 (5.28 g, 5 mmol) in a mixture of MeOH (25 mL) an 2 N HCl (50 mL) was refluxed for 6 h, during which most of the solid dissolved. A small amount of insoluble tar was filtered off, the MeOH was evaporated under reduced pressure, and the residue was extracted with EtOAc. Evaporation of the EtOAc extract and recrystallization from H$_2$O containing a small amount of EtOH afforded 8 as a yellow powder (2.49 g, 65%) which was used directly in the next step; mp 109–110° C. (lit. mp 111–113° C.; TLC; $R_f$ 0.2 (silica gel, 2:1 isooctane-EtOAc).

Step 4. A solution of 8 (760 mg, 5 mmol) and $K_2CO_3$ (828 mg, 6 mmol) in dry DMSO (5 mL) was treated with 1-bromopentane (744 μL, 906 mg, 6 mmol). After 20 h at room temperature and then 10 min at 60° C., the mixture was diluted with $H_2O$ and extracted with EtOAc. Evaporation under reduced pressure left a solid (1.1 g), which was chromatographed on silica gel (15 g, 2×12 cm) with 2:1 isooctane-EtOAc as the eluent. Appropriately pooled fractions were evaporated to obtain 2-methoxy-5-pentyloxybenzaldehyde (9) as a yellow oil (1.12 g, 100%); TLC: bluish spot, $R_f$ 0.6 (silica gel, 2:1 isooctane-EtOAc); IR (thin film) v 2960, 2930, 2870, 2750, 1680, 1605, 1580, 1495, 1425 cm$^{-1}$; $^1$H NMR (200 MHz, CDCl$_3$) δ 0.85 (m, 3H, pentyl Me), 1.35 (m, 4H, pentyl 3- and 4-CH$_2$), 1.73 (p, J=7 Hz, 2H, pentyl 2-Me), 3.85 (s, 3H, MeO), 3.90 (t, J=7 Hz, 2H, OCH$_2$), 6.90 (d, J=9 Hz, 1H, aryl H-3), 7.09 (dd, J=9 Hz, J=3 Hz, 1H, aryl H-4), 7.28 (d, J=3 Hz, 1H, aryl H-6), 10.40 (s, 1H, CH=O).

EXAMPLE 2

2,4-Diamino-5-(2-methoxy-5-pentyloxybenzyl)pyrimidine (Scheme 1, Compound 3a).

Step 1. A solution of NaOMe was prepared by dissolving clean metallic Na (23 mg, 1 mmol) in absolute MeOH (3 mL). The solvent was evaporated under reduced pressure, the solid was taken up in DMSO (1.5 mL), and to the solution was added 3-morpholinopropionitrile (728 mg, 5.2 mmol). The solution was placed in an oil bath at 100° C., and to it was slowly added a solution of 9 (1.05 g, 4.73 mmol) in DMSO (1.5 mL). After 20 min of heating, the reaction mixture was cooled and partitioned between EtOAc and $H_2O$ that had been slightly acidified with dilute aqueous citric acid to prevent the formation of an emulsion. TLC analysis (silica gel, 1:1 isooctane-EtOAc) showed an $I_2$-absorbing spot with $R_f$ 0.3 (not UV-absorbing), along with a major UV-absorbing spot ($R_f$ 0.4) corresponding to the product (10) and a faint UV-absorbing impurity ($R_f$ 0.7). Flash chromatography on silica gel (20 g, 2×17 cm) afforded 2-(2-methoxy-5-pentyloxybenzyl)-3-morpholinoacrylonitrile (10) as a yellow gum which was used directly the next step; yield 1.16 g (71%); $^1$H NMR (200 MHz, CDCl$_3$) δ 0.88 (m, 3H, pentyl CH$_3$), 1.41 (m, 4H, pentyl 3- and 4-CH$_2$), 1.75 (p, J=7 Hz, 2H, pentyl 2-CH$_2$), 3.0–3.8 (m, 15H, morpholine CH$_2$, MeO, pentyl OCH$_2$, and benzylic CH$_2$), 6.79 (m, 4H, vinyl and aryl protons).

Step 2. A solution of 10 (0.835 g, 2.43 mmol) and aniline hydrochloride (0.47 g, 3.64 mmol) in absolute EtOH (10 mL) was refluxed for 1 h. In a separate flask, guanidine hydrochloride (1.09 g, 11.4 mmol) was added to a solution of NaOEt prepared by dissolving clean metallic Na (345 mg, 15 mmol) in absolute EtOH (15 mL) and the flask was swirled manually for 5 min. The entire contents of the second flask (including the NaCl) were added to the first, and the combined mixture was refluxed for 18 h and then filtered while hot. TLC analysis of the filtrate (silica gel, 10:1 EtOAc-MeOH) showed the product (3a) as a major UV-absorbing spot ($R_f$ 0.3), along with several fast-moving impurities. Flash chromatography (silica gel, 18 g, 2×15 cm) with 10:1 EtOAc-MeOH as the eluent afforded an amorphous solid, which on recrystallization from aqueous EtOH afforded 3a as white flakes (540 mg, 70%); mp 140–141° C.; IR (KBr) v 3410, 3330, 3230, 3120, 2990, 2950, 2910sh, 2870, 2830, 1665, 1635, 1605, 1565, 1540, 1505, 1480, 1460, 1440, 1420 cm$^{-1}$; $^1$H NMR (200 MHz, DMSO-d$_6$) δ 0.87 (m, 3H, pentyl Me), 1.33 (m, 4H, pentyl 3- and 4-CH$_2$), 1.64 (p, J=7 Hz, 2H, pentyl 2-CH$_2$), 3.47 (s, 2H, bridge CH$_2$), 3.73 (s, 3H, OMe), 3.83 (t, J=7 Hz, 2H, OCH$_2$), 5.65 (broad s, 2H, NH$_2$), 6.02 (br s, 2H, NH$_2$), 6.64 (d, J=3 Hz, 1H, aryl H-6), 6.70 (dd, J=8 Hz, J=3H, 1H, aryl H-4), 6.87 (d, J=8 Hz, 1H, aryl H-3), 7.39 (s, 1H, pyrimidine H-6).

EXAMPLE 3

General Procedure for a more Direct Synthesis of 2,4-Diamino-5-(2-methoxy-5-alkoxybenzyl)pyrimidines (Scheme 2)

Step 1. Compound 8 (1.05 g, 5 mmol) was added to a solution of NaOMe prepared by dissolving clean metallic Na (115 mg, 5 mmol) in absolute MeOH (5 mL). After 5 min, the intensely yellow solution of the Na salt 12 was evaporated to dryness and the residue was triturated with Et$_2$O until a solid formed. The Et$_2$O was decanted and the powder dried with aid of a vacuum pump and taken up in DMSO (5 mL). The alkyl halide (5 mmol) was then added and the solution allowed to stand at room temperature overnight. In a separate flask, 3-morpholinopropionitrile (700 mg, 5 mmol) was added to a solution of freshly prepared NaOMe (1 mmol) in DMSO (2 mL), and the mixture was placed in an oil bath pre-heated to 100° C. To this solution were then added the contents of the first flask, and the combined reaction mixture was heated for 20 min. After being cooled to room temperature, the mixture was partitioned between EtOAc and dilute aqueous citric acid. TLC analysis of the organic layer gave predominantly one spot with an $R_f$ of ca. 0.5 (silica gel, 1:1 EtOAc-isooctane), corresponding to the desired 2-arylmethyl-3-morpholinoacrylonitrile. The EtOAc was evaporated and replaced with absolute EtOH (20 mL) and, after addition of aniline hydrochloride (0.97 g, 7.5 mmol), the mixture was refluxed for 1 h. Separately, guanidine hydrochloride (1.19 g, 12.5 mmol) was added to a solution of NaOEt obtained by dissolving Na metal (460 mg, 20 mmol) in absolute EtOH (15 mL). After being stirred for 5 min, the contents of the flask (including the precipitated NaCl) were transferred to the flask containing the 2-arylmethyl-3-anilinoacrylonitrile. The mixture was refluxed for 20 h and filtered while hot, and the product was isolated and purified in the same way as 3a (see above). The following analogs were prepared by this general method:

EXAMPLE 4

2,4-Diamino-5-(2-methoxy-5-hexyloxybenzyl)pyrimidine (Scheme 2, Compound 3b):

Yield 950 mg (58%); glistening white plates, mp 139–140° C.; IR (KBr) v 3430, 3330, 3250, 3130, 3010, 2950, 2870, 1675, 1645, 1610, 1575, 1545, 1510, 1490, 1475, 1450, 1435, 1400 cm$^{-1}$; $^1$H NMR (200 MHz, DMSO-d$_6$) δ 0.86 (t, J=7 Hz, 3H, hexyl Me), 1.30 (m, 6H, hexyl 3- to 5-CH$_2$), 1.64 (p, J=7 Hz, 2H, hexyl 2-CH$_2$), 3.47 (s, 2H, bridge CH$_2$), 3.73 (s, 3H, OMe), 3.83 (t, J=7 Hz, 2H, OCH$_2$), 5.65 (br s, 2H, NH$_2$), 6.02 (br s, 2H, NH$_2$), 6.64 (d, J=3 Hz, 1H, aryl H-3), 7.39 (s, 6), 6.70 (dd, J=8 Hz, J=3 Hz, 1H, aryl H-4), 6.87 (d, J=8 Hz, 1H, aryl H-3), 7.39 (s, 1H, pyrimidine H-6).

EXAMPLE 5

2,4-Diamino-5-(2-methoxy-5-heptyloxybenzyl)pyrimidine (Scheme 2, Compound 3c):

Yield 1.09 mg (63%); glistening white plates, mp 134–135° C.; IR (KBr)ν 3400, 3310, 3210, 3110, 2990, 2920, 2850, 1665, 1635, 1605, 1575, 1540, 1500, 1485, 1455, 1440, 1415 cm$^{-1}$; $^1$H NMR (200 MHz, DMSO-d$_6$) δ 0.86 (t, J=7 Hz, 3H, heptyl Me), 1.28 (m, 8H, heptyl 3- to 6-CH$_2$), 1.65 (p, J=7 Hz, 2H, heptyl 2-CH$_2$), 3.47 (s, 2H, bridge CH$_2$), 3.73 (s, 3H, OMe), 3.83 (t, J=7 Hz, 2H, OCH$_2$), 5.66 (br s, 2H, NH$_2$), 6.03 (br s, 2H, NH$_2$), 6.65 (d, J=3 Hz, 1H, aryl H-6), 6.72 (dd, J=8 Hz, J=3 Hz, 1H, aryl H-4), 6.87 (d, J=8 Hz. IH, aryl H-3), 7,40 (s, 1H, pyrimidine H-6).

EXAMPLE 6

2,4-Diamino-5-(2-methoxy-5-octyloxybenzyl)pyrimidine (Scheme 2, Compound 3d):

Yield 1.03 mg (58%); mp 135–136° C.; IR (KBr)ν 3400, 3300, 3110, 2980, 2910, 2840, 1660, 1645, 1600, 1565, 1535, 1500, 1480, 1455, 1435, 1415 cm$^{-1}$; $^1$H NMR (200 MHz, DMSO-d$_6$) δ 0.85 (t, J=7 Hz, 3H, octyl Me), 1.27 (m, 10H, octyl 3- to 7-CH$_2$), 1.66 (p, J=7 Hz, 2H, octyl 2-CH$_2$), 3.49 (s, 2H, bridge CH$_2$), 3.75 (s, 3H, OMe), 3.85 (t, J=7 Hz, 2H, OCH$_2$), 5.67 (br s, 2H, NH$_2$), 6.05 (br s, 2H, NH$_2$), 6.66 (d, J=3 Hz, 1H, aryl H-6), 6.74 (dd, J=8 Hz, J=3 Hz, 1H, aryl H-4), 6.88 (d, J=8 Hz, 1H, aryl H-3), 7.41 (s, 1H, pyrimidine H-6).

EXAMPLE 7

2,4-Diamino-5-(2-methoxy-5-nonyloxybenzyl)pyrimidine (Scheme 2, Compound 3e):

Yield 877 mg (47%); mp 134–135° C.; IR (KBr)ν 3410, 3320, 3120, 2920, 2850, 1665, 1635, 1605, 1565, 1540, 1500, 1485, 1455, 1440, 1420 cm$^{-1}$; $^1$H NMR (200 MHz, DMSO-d$_6$) δ 0.86 (t, J=7 Hz, 3H, nonyl Me), 1.25 (m, 12H, nonyl 3- to 8-CH$_2$), 1.64 (p, J=7 Hz, 2H, nonyl 2-CH$_2$), 3.47 (s, 2H, bridge CH$_2$), 3.74 (s, 3H, OMe). 3.83 (t, J=7 Hz, 2H, OCH$_2$), 5.65 (br s, 2H, NH$_2$), 6.03 (br s, 2H, NH$_2$), 6.65 (d, J=3 Hz, 1H, aryl H-6), 6.72 (dd, J=8 Hz, J=3 Hz, 1H, aryl H-4), 6.88 (d, J=8 Hz, 1H, aryl H-3), 7.40 (s, 1H, pyrimidine H-6).

EXAMPLE 8

2,4-Diamino-5-[2-methoxy-5-(4-benzyloxy)benzyl]pyrimidine (Scheme 2, Compound 14a).

This compound was prepared by the same procedure as 3b–e except that the scale was increased twofold, the alkylation step with benzyl bromide was performed in MeOH instead of DMSO, and the reaction mixture was refluxed for 18 h. Yield 1.99 g (59%); beige powder, mp 157–158° C.; IR (KBr)ν 3510, 3480, 3420, 3360, 3300, 3160, 3110, 3050, 3030, 1675, 1640, 1605, 1575, 1505, 1460 cm$^{-1}$; $^1$H NMR (200 MHz, DMSO-d$_6$) δ 3.49 (s, 2H, bridge CH$_2$), 3.74 (s, 3H, OMe), 4.99 (s, 2H, OCH$_2$), 5.67 (br s, 2H, NH$_2$), 6.05 (br s, 2H, NH$_2$), 6.75–6.95 (m, 3H, aryl protons on the anisole), 7.40 (m, 6H, pyrimidine H-6 and aryl protons on the benzyloxy group).

EXAMPLE 9

2-Methoxy-4-[(4-methoxybenzyl)oxy]benzaldehyde (Scheme 2, Compound 13b).

Compound 8 (2.10 g, 0.01 mol) was added to a solution of NaOMe prepared by dissolving metallic Na (0.23 g, 0.01 mol) in absolute MeOH (40 mL). After 5 min, the solvent was evaporated and the residue triturated with Et$_2$O until a powder formed, at which point the Et$_2$O was decanted. The powder was dried in vacuo and taken up in dry DMF (2 mL), and to the solution was added 4-methoxybenzyl chloride (freshly synthesized from 4-methoxybenzyl alcohol and SOCl$_2$ in toluene). After 20 h at room temperature, the DMF was evaporated under reduced pressure and the residue was partitioned between EtOAc and 1 N NaOH. The organic layer was evaporated, and the residue was recrystallized from EtOH-H$_2$O. Drying in a lyophilization apparatus afforded 13b as a white powder (1.91 g, 70%); mp 75–76° C.; TLC: bluish spot, R$_f$ 0.4 (silica gel, 2:1 isooctane-EtOH); IR (KBr)ν 2970, 2940, 2840, 1675, 1610, 1585, 1515, 1490, 1465, 1450, 1435, 1425 cm$^{-1}$; $^1$H NMR (200 MHz, CDCl$_3$) δ 3.82 (s, 3H, OMe), 3.90 (s, 3H, OMe), 4.98 (s, 2H benzylic CH$_2$), 6.91 (m, 4H, aryl protons of 4-methoxybenzyl group), 7.18 (dd, J=8 Hz, J=3 Hz, 1H, benzaldehyde H-4), 7.35 (d, J=8 Hz, 1H, benzaldehyde H-3), 7.42 (d, J=3 Hz, 1H, benzaldehyde H-6), 10.44 (s, 1H, CH=O).

EXAMPLE 10

2,4-Diamino-5-[2-methoxy-5-(4-methoxybenzyloxy)benzyl]pyrimidine (Scheme 2, Compound 14b).

This compound was prepared from 13b in 61% yield via the general procedure described above for 3b–e; white powder, mp 220–221° C.; IR (KBr)ν 3480, 3410, 3340, 3250, 3120, 2950, 3120, 2960, 2920, 2830, 1665, 1620, 1595, 1565, 1510, 1495, 1450, 1415 cm$^{-1}$; $^1$H NMR (DMSO-d$_6$) δ 3.48 (br s, >2H, bridge CH$_2$ and partial H$_2$O of solvation), 3.74 (s, 3H, OMe), 3.75 (s, 3H, OMe), 4.89 (s, 2H, OCH$_2$), 5.66 (br s, 2H, NH$_2$), 6.04 (br s, 2H, NH$_2$), 6.72–7.00 (m, 5H, aryl protons), 7.33 (d, J=8 Hz, 2H, aryl protons), 7.40 9s, 1H, pyrimidine H-6).

EXAMPLE 11

2,4-Diamino-5-(2-methoxy-5-hydroxybenzyl)pyrimidine (Scheme 2, Compound 15).

A stirred suspension of 14b (183 mg, 0.5 mmol) in MeOH (5 mL) was treated with TsOH.H$_2$O (190 mg, 1 mmol), whereupon the solids dissolved and new precipitate formed quickly The solution was left at room temperature for two days, after which the solvent was evaporated and the residue was suspended in H$_2$O. The mixture was adjusted to pH>10 with NaOH, a trace of insoluble material was filtered, and the filtrate was applied onto a column of Dowex 50W-X2 resin (H$^+$ form, 1.5×15 cm). The column was washed with H$_2$O until the eluent was neutral and UV-transparent, and then with 1.5% NH$_4$OH to remove the product. Appropriately pooled fractions were concentrated and freeze-dried to obtain 15 as a light-brown powder (110 mg, 89%); TLC: R$_f$ 0.2 (silica gel, 5:1 EtOAc-MeOH). The analytical sample was prepared by recrystallization from EtOH-H$_2$O; mp 216–218° C. dec; IR (KBr)ν 3430, 3350, 3210, 3050, 2960, 2930, 2830, 2680w, 2500br, 1665sh, 1640, 1615, 1605sh, 1565, 1540, 1505, 1470, 1445 cm$^{-1}$; $^1$H NMR (200 MHz, DMSO-$d_6$) δ 3.45 (s, 2H, benzylic CH$_2$), 3.71 (s, 3H, OMe), 5.66 (br s, 2H, NH$_2$), 6.00 (br s, 2H, NH$_2$), 6.44 (d, J=3 Hz, 1H, aryl H-6), 6.54 (dd, J=8 Hz, J=3 Hz, 1H, aryl 4-H), 6.78 (d, J=8 Hz, 1H, aryl H-3), 7.39 (s, 1H, pyrimidine H-6), 8.80 (s, 1H, phenolic OH). The presence of a small amount of EtOH in the sample was indicated by a small triplet at δ 1.05.

EXAMPLE 12

General Procedure for the Synthesis of 2,4-Di-amino-5-[2-methoxy-5-[2-methoxy-5-(ω-carboxy-alkoxy)benzyl]pyrimidines 3f–k.

Clean metallic Na (23 mg (1.0 mmol) was dissolved in absolute EtOH (2 mL), the solvent was evaporated under reduced pressure, and the residue was re-dissolved in DMSO (3 mL). To this solution was then added trimethoprim, 1.5 (246 mg, 1.0 mmol), and after the reaction mixture was stirred at room temperature for 30 min the bromo ester (1.0 mmol) was added in a single portion. TLC analysis (silica gel, 5:1 EtOAc-MeOH) revealed gradual loss of the spot with $R_f$ 0.2 (unreacted 15) and its replacement by a faster-moving spot with $R_f$ 0.4. The reaction was typically over in 2 h. The product was saponified instantaneously upon addition of 2 N NaOH (1.5 mL) followed by addition of H$_2$O to a final volume of ca. 60 mL. Any insoluble material remaining at this point was filtered off, and the clear solution was applied onto a column of Dower 50W-X2 (H$^+$ form, 2×20 cm). The column was washed with H$_2$O until the eluate was neutral and UV-transparent, and then with 1.5% NH$_4$OH to remove the product. Appropriately pooled eluates were concentrated to dryness by rotary evaporation followed by lyophilization. The solid was re-dissolved in H$_2$O with a small volume of dilute NH$_4$OH added as needed, and was re-precipitated with 10% AcOH. The collected product was then dried and analyzed. Microchemical analyses typically indicated the presence of fractional amounts of AcOH or H$_2$O of solvation despite careful drying in vacuo over P$_2$O$_5$. The following compounds were obtained in this manner.

EXAMPLE 13

2,4-Diamino-5-[(2-methoxy-5-(3-carboxypropyloxy)benzyl]pyrimidine (Scheme 2, Compound 3f):

White solid (19% yield), mp 244–246° C.; IR (KBr)ν 3340, 3210, 2960 (broad underlying absorbance at 3600–2450), 1665, 1650, 1630sh, 1565, 1505, 1465, 1410 cm$^{-1}$; $^1$H NMR (200 MHz, DMSO-$d_6$) δ 1.87 (m, 2H, CH$_2$CH$_2$CH$_2$), 2.32 (t, J=7 Hz, 2H, CH$_2$COOH), 3.47 (s, benzylic CH$_2$ partially overlapping a broad H$_2$O peak), 3.72 (s, OMe partially overlapping H$_2$O), 3.84 (t, J=6 Hz, OCH$_2$ partially overlapping H$_2$O), 5.66 (br s, 2H, NH$_2$), 6.03 (br s, 2H, NH$_2$), 6.68 (m, 2H, aryl H-4 and H-6), 6.87 (d, J=8 Hz, aryl H-3), 7.37 (s, 1H, pyrimidine H-6).

EXAMPLE 14

2,4-Diamino-5-[(2-methoxy-5-(4-carboxybutyloxy)benzyl]pyrimidine (Scheme 2, Compound 3g):

Beige solid (65% yield), mp 94–100° C.; IR (KBr)ν 3340, 3170, 2940 (broad underlying absorbance at 3400–2700), 1655, 1500, 1460 cm$^{-1}$; $^1$H NMR (200 MHz, DMSO-$d_6$) δ 1.64 (m, 4H, CH$_2$(CH$_2$)$_2$CH$_2$), 2.32 (t, J=7 Hz, 2H, CH$_2$COOH), 3.46 (s, benzylic CH$_2$), 3.72 (s, 3H, OMe), 3.83 (t, J=6 Hz, 2H, OCH$_2$), 5.75 (br s, 2H, NH$_2$), 6.12 (br s, 2H, NH$_2$), 6.60 (d, J=3 Hz, 1H, aryl H-6), 6.73 (dd, J=8 Hz, J=3 Hz, 1H, aryl H-4), 6.87 (d, J=8 Hz, 1H, aryl H-3), 7.37 (s, 1H, pyrimidine H-6). This compound was purified on DEAE-cellulose (HCO$_3^-$ form), but this method was less effective than the use of Dowex 50W-X2 (H$^+$ form) due to precipitation on the column. The presence of AcOH was indicated by a singlet at δ 1.89.

EXAMPLE 15

2,4-Diamino-5-[(2-methoxy-5-(5-carboxypentyloxy)benzyl]pyrimidine (Scheme 2, Compound 3h):

Beige powder (85% yield), mp 100–104° C.; IR (KBr)ν 3330, 3190, 2930, 2860 (broad underlying absorbance at 3500–2400), 1655, 1560, 1495, 1455 cm$^{-1}$; $^1$H NMR (200 MHz, DMSO-$d_6$) δ 1.30–1.70 (m, 6H, CH$_2$(CH$_2$)$_3$CH$_2$), 2.19 (t, J=7 Hz, 2H, CH$_2$COOH), 3.46 (s, 2H, benzylic CH$_2$), 3.72 (s, 3H, OMe), 3.82 (t, J=6 Hz, 2H, OCH$_2$), 5.66 (br s, 2H, NH$_2$), 6.03 (br s, 2H, NH$_2$), 6.64 (d, J=3 Hz, 1 H, aryl H-6), 6.72 (dd, J=8 Hz, J=3 H, 1H, aryl H-4), 6.86 (d, J=8 Hz, 1H, aryl H-3), 7.38 (s, 1H, pyrimidine H-6). The presence of AcOH of was indicated by a singlet at δ 1.89.

EXAMPLE 16

2,4-Diamino-5-[(2-methoxy-5-(6-carboxyhexyloxy)benzyl]pyrimidine (Scheme 2, Compound 3i):

Light-brown powder (77% yield), mp 200–202° C.; IR (KBr)ν 3330, 3190, 2930, 2850 (broad underlying absorbance at 3500–2700), 1655, 1555, 1535, 1495, 1455 cm$^{-1}$; $^1$H NMR (200 MHz, DMSO-$d_6$) δ 1.32–1.63 (m, 8H, CH$_2$(CH$_2$)$_4$CH$_2$), 2.19 (t, J=7 Hz, 2H, CH$_2$COOH), 3.46 (s, benzylic CH$_2$ partially overlapping a broad H$_2$O peak), 3.72 (s, OMe partially overlapping H$_2$O), 3.82 (t, 2H, J=6 Hz, OCH$_2$), 5.69 (br s, 2H, NH$_2$), 6.06 (br s, 2H, NH$_2$), 6.64 (d, J=3 Hz, 1H, aryl H-6), 6.72 (dd, J=8 Hz, J=3 H, 1H, aryl H-4), 6.86 (d, J=8 Hz, 1H, aryl H-3), 7.38 (s, 1H, pyrimidine H-6).

EXAMPLE 17

2,4-Diamino-5-[(2-methoxy-5-(7-carboxyheptyloxy)benzyl]pyrimidine (Scheme 2, Compound 3j):

Light-brown powder (74% yield), mp 108–112° C.; IR (KBr)ν 3330, 3180, 2920, 2850 (broad underlying absorbance at 3500–2700), 1655, 1525sh, 1495, 1460 cm$^{-1}$; $^1$H NMR (200 MHz, DMSO-$d_6$) δ1.29-1.62 (m, 10H, CH$_2$(CH$_2$)$_5$CH$_2$), 2.17 (t, J=7 Hz, 2H, CH$_2$COOH), 3.46 (s, 2H, benzylic CH$_2$), 3.72 (s, 3H, OMe), 3.82 (t, 2H, J=6 Hz, OCH$_2$), 5.71 (br s, 2H, NH$_2$), 6.08 (br s, 2H, NH$_2$), 6.66 (d, J=3 Hz, 1H, aryl H-6), 6.73 (dd, J=8 Hz, J=3 H, 1H, aryl H-4), 6.86 (d, J=8 Hz, 1H, aryl H-3), 7.38 (s, 1H, pyrimidine H-6). The presence of AcOH in the sample was indicated by a singlet at δ 1.89.

EXAMPLE 18

2,4-Diamino-5-[(2-methoxy-5-(7-carboxyheptyloxy)benzyl]pyrimidine (Scheme 2, Compound 3k):

Light-brown powder (80% yield), mp 142–144° C.; IR (KBr)ν 3330, 3190, 2920, 2850 (broad underlying absorbance at 3500–2700), 1655, 1555, 1495, 1460 cm$^{-1}$; $^1$H NMR (200 MHz, DMSO-$d_6$) δ 1.25–1.63 (m, 12H, $CH_2(CH_2)_6CH_2$), 2.17 (t, J=7 Hz, 2H, $CH_2COOH$), 3.47 (s, benzylic $CH_2$ partially overlapping a broad $H_2O$ peak), 3.72 (s, OMe, partially overlapping $H_2O$), 3.82 (t, $OCH_2$ partially overlapping $H_2O$), 5.73 (br s, 2H, $NH_2$), 6.09 (br s, 2H, $NH_2$), 6.68 (d, J=3 Hz, 1H, aryl H-6), 6.73 (dd, J=8 Hz, J=3 H, 1H, aryl H-4), 6.88 (d, J=8 Hz, 1H, aryl H-3), 7.38 (s, 1H, pyrimidine H-6). The presence of AcOH in the sample was indicated by a singlet at δ 1.90.

EXAMPLE 19

Combustion Analysis.

Standard C,H,N elemental analysis was carried out on compositions prepared supra

| Cmpd | Empirical Formula | Calcd, % | | | Found, % | | |
|---|---|---|---|---|---|---|---|
| | | C | H | N | C | H | N |
| 3a | $C_{17}H_{24}N_4O_2$ | 64.53 | 7.65 | 17.71 | 64.47 | 7.66 | 17.60 |
| 3b | $C_{18}H_{26}N_4O_2$ | 65.43 | 7.93 | 16.96 | 65.46 | 8.03 | 16.82 |
| 3c | $C_{19}H_{28}N_4O_2$ | 66.25 | 8.19 | 16.27 | 66.31 | 8.29 | 16.11 |
| 3d | $C_{20}H_{30}N_4O_2$ | 67.01 | 8.43 | 15.63 | 67.17 | 8.44 | 15.48 |
| 3e | $C_{21}H_{32}N_4O_2$ | 67.71 | 8.66 | 15.04 | 67.76 | 8.71 | 14.87 |
| 3f | $C_{16}H_{20}N_4O_3.3.2H_2O$ | 49.28 | 6.82 | 14.37 | 49.37 | 6.57 | 14.08 |
| 3g | $C_{17}H_{22}N_4O_4.0.75AcOH.0.5H_2O$ | 55.49 | 6.54 | 13.99 | 55.71 | 6.22 | 14.08 |
| 3h | $C_{18}H_{24}N_4O_4.0.5AcOH$ | 58.45 | 6.71 | 14.35 | 58.42 | 6.49 | 14.42 |
| 3i | $C_{19}H_{26}N_4O_4.0.75AcOH$ | 58.82 | 7.14 | 14.44 | 59.02 | 6.91 | 14.18 |
| 3j | $C_{20}H_{28}N_4O_4.0.75AcOH-0.25H_2O$ | 58.96 | 7.25 | 12.79 | 58.76 | 6.93 | 12.62 |
| 3k | $C_{21}H_{30}N_4O_4.0.5AcOH.0.25H_2O$ | 60.46 | 7.50 | 12.82 | 60.41 | 7.11 | 12.78 |
| 12 | $C_{13}H_{18}O_3$ | 70.25 | 8.16 | | 70.34 | 8.15 | |
| 13b | $C_{16}H_{16}O_4$ | 70.58 | 5.92 | | 70.63 | 5.96 | |
| 14a | $C_{19}H_{20}N_4O_2$ | 67.84 | 5.99 | 16.66 | 67.84 | 6.05 | 16.34 |
| 14b | $C_{20}H_{22}N_4O_3.0.25H_2O$ | 64.76 | 6.11 | 15.10 | 64.36 | 6.04 | 15.49 |
| 15 | $C_{12}H_{14}N_4O_2.0.2EtOH$ | 58.30 | 6.00 | 21.93 | 58.40 | 5.73 | 21.84 |

Although a preferred embodiment of the invention has been described using specific terms, such description is for illustrative purposes only, and it is to be understood that changes and variations may be made without departing from the spirit or scope of the following claims.

All references disclosed herein are incorporated by reference.

What is claimed is:

1. A compound according to Formula I:

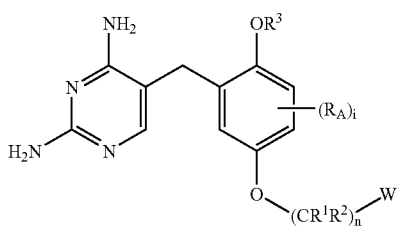

wherein:

$R_A$ is Independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, chloro, fluoro, $C_{1-4}$fluoroalkyl, amino, mono and di($C_{1-4}$alkyl) amino, nitrile, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio, optionally substituted aryl acetoxy or optionally substituted heteroaryl acetoxy;

$R^1$ and $R^2$ are independently selected at each occurrence or $R^1$, and $R^2$ in Formula I from the group consisting of hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio;

$R^3$ is selected from the group consisting of hydrogen, $C_{1-6}$alkyl, $C_{2-6}$alkenyl, $C_{2-6}$alkynyl, and $C_{1-6}$fluoroalkyl;

W is hydroxyl, alkoxy, amino, carboxylate, $C_{1-6}$alkylcarbonyloxy, sulfonate or carhoxamide;

i is an integer from 0 to 3; and n Is an integer from about 1 to about 12.

2. A compound according to claim 1 wherein $R_A$ is hydrogen at each occurrence of $R_A$, in Formula I.

3. A compound according to claim 1 of the Fomiula II:

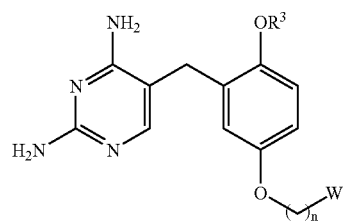

wherein

W is hydroxy or carboxylate;

$R^3$ is a $C_{1-4}$alkyl group; and n is an integer from 3 to 8.

4. A compound of any one of claims 1 through 3 where W is carboxylate.

5. A compound according to Formula III:

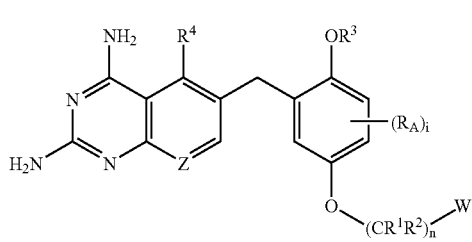

wherein:
- $R_A$ is independently selected at each occurrence of $R_A$ from the group consisting of hydrogen, $C_{1-6}$alkyl, $C_{2-6}$alkenyl, $C_{2-6}$alkynyl, $C_{3-8}$cycloalkyl, $C_{1-6}$alkoxy, chloro, fluoro, $C_{1-4}$fluoroalkyl, amino, mono and di($C_{1-6}$alkyl)amino, nitrile, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio, optionally substituted aryl acetoxy or optionally substituted heteroaryl acetoxy;
- $R^1$, $R^2$, and $R^4$ are independently selected at each occurrence of $R^1$, $R^2$, and $R^4$ in Formula III from the group consisting of hydrogen, $C_{1-6}$alkyl, $C_{2-6}$alkenyl, $C_{2-6}$alkynyl, chloro, fluoro, $C_{1-6}$fluoroalkyl, $C_{1-6}$alkoxy, optionally substituted aryloxy, optionally substituted heteroaryloxy, optionally substituted aryl, optionally substituted heteroaryl, optionally substituted arylamino, optionally substituted heteroarylamino, $C_{1-6}$alkylthio, optionally substituted arylthio, optionally substituted heteroarylthio;
- $R^3$ is selected from the group consisting of hydrogen, $C_{1-6}$alkyl, $C_{2-6}$alkenyl, $C_{2-5}$alkynyl, and $C_{1-6}$fluoroalkyl;
- W is hydroxy, alkoxy, amino, carboxylate, $C_{1-6}$alkylcarbonyloxy or carboxamide;
- Z is N or CH;
- i is an integer from 0 to 5; and
- n is an integer from 1 to 12.

6. A compound according to claim 5, wherein $R_A$ is hydrogen at each occurrence of $R_A$ i n Formula III.

7. A compound according to claim 5, of the Formula IV

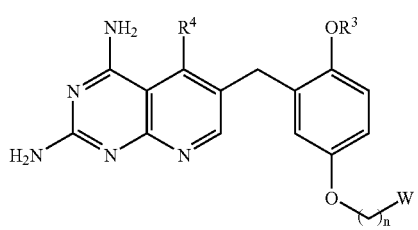

wherein
- W is hydroxy or carboxylate;
- $R^3$ is a $C_{1-4}$alkyl group;
- $R^4$ is hydrogen, chloro, methoxy or methyl; and
- n is an integer from 3 to 8.

8. A compound according to claim 5, of the Formula V

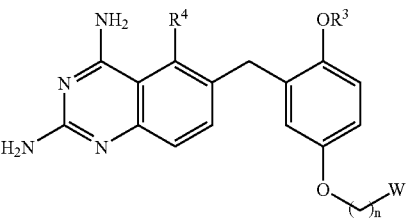

wherein
- W is hydroxy or carboxylate;
- $R^3$ is a $C_{1-4}$alkyl group;
- $R^4$ is hydrogen, chloro, methoxy or methyl; and
- n is an Integer from 3 to 8.

9. A compound of any one of claims 5 through 8 where W is carboxylate.

10. A compound of claim 1 or claim 5, wherein the compound has an $IC_{50}$ of 50 μM or less against a DHFR enzyme of an organism selected from the group consisting of organisms causing malaria, trypanosomiasis, leprosy, toxoplasmosis, and pneumocystis carinii pneumonia.

11. A compound of claim 10, wherein the organism is selected from the group consisting of *Pneumocystis carinii, Toxoplasma gondii,* and *Mycobacterium avium*.

12. A compound according to claim 1 or claim 5, wherein a binding selectivity of the compound is about 1, wherein the binding selectivity is a ratio of the compound's $IC_{50}$ for binding mammalian DHFR enzymes to the compound's $IC_{50}$ for binding to a DHFR enzyme of an organism selected from the group consisting of organisms causing malaria, trypanosomiasis, leprosy, toxoplasmosis, and pneumocystis carinii pneumonia.

13. A compound according to claim 12, where the binding selectivity of the compound is about 2.

14. A compound according to claim 12, where the binding selectivity of the compound is about 4.

15. A compound according to claim 12, where the binding selectivity of the compound is about 8.

16. A compound according to claim 12, where the binding selectivity of the compound is about 16.

17. A compound according to claim 12, where the binding selectivity of the compound is about 20.

18. A compound according to claim 12, where the binding selectivity of the compound is about 50.

19. A pharmaceutical composition comprising a compound of claim 1 or claim 5, and a pharmaceutically acceptable carrier.

20. A method for treating a mammal suffering or susceptible to an infection or disorder selected from the group consisting of trypanosomiasis, toxoplasmosis, and pneumocystis carinii pneumonia, comprising administering to the mammal an effective amount of a compound or composition of claim 1 or claim 5.

21. A method of claim 20 wherein the mammal is immuno-compromised.

22. The method of claim 20, wherein the mammal is a HIV-positive human.

23. The method of claim 20, wherein the mammal is suffering from an acquired immune deficiency disorder.

24. The method of claim 20, wherein the mammal is suffering from an autoimmune disorder or disease.

25. The method of claim 20, wherein the infection is a *Pneumocystis carinii* (Pc), *Toxoplasma gondii* or *Mycobacterium avium* infection.

26. A compound of claim 10, wherein the compound has an $IC_{50}$ of 25 μM or less against the DHFR enzyme.

27. A compound of claim 10, wherein the compound has an $IC_{50}$ of 10 μM or less against the DHFR enzyme.

28. A compound of claim 10, wherein the compound has an $IC_{50}$ of 5 μM or less against the DHFR enzyme.

29. A compound of claim 10, wherein the compound has an $IC_{50}$ of 1 μM or less against the DHFR enzyme.

30. A compound of claim 10, wherein the compound has an $IC_{50}$ of 0.5 μM or less against the DHFR enzyme.

* * * * *